(12) United States Patent
Bonadio et al.

(10) Patent No.: US 8,657,741 B2
(45) Date of Patent: *Feb. 25, 2014

(54) WOUND RETRACTOR

(75) Inventors: Frank Bonadio, Bray (IE); John Butler, Blackrock (IE); Catherine Deegan, Clontarf (IE); Trevor Vaugh, Birr (IE)

(73) Assignee: Atropos Limited, County Wicklow (IE)

( * ) Notice: Subject to any disclaimer, the term of this patent is extended or adjusted under 35 U.S.C. 154(b) by 0 days.

This patent is subject to a terminal disclaimer.

(21) Appl. No.: 13/210,307

(22) Filed: Aug. 15, 2011

(65) Prior Publication Data

US 2012/0123214 A1 May 17, 2012

Related U.S. Application Data

(63) Continuation of application No. 11/486,383, filed on Jul. 14, 2006, now Pat. No. 8,021,296, which is a continuation-in-part of application No. 10/678,653, filed on Oct. 6, 2003, now Pat. No. 7,559,893.

(60) Provisional application No. 60/415,780, filed on Oct. 4, 2002, provisional application No. 60/428,215, filed on Nov. 22, 2002, provisional application No. 60/490,909, filed on Jul. 30, 2003, provisional application No. 60/699,371, filed on Jul. 15, 2005, provisional application No. 60/724,785, filed on Oct. 11, 2005.

(51) Int. Cl.
*A61B 1/32* (2006.01)

(52) U.S. Cl.
USPC .......................................... 600/208

(58) Field of Classification Search
USPC .......................... 606/108; 600/201, 203, 208; 604/167.03
See application file for complete search history.

(56) References Cited

U.S. PATENT DOCUMENTS

| 1,157,202 A | 10/1915 | McLeland |
| 1,598,284 A | 8/1926 | Kinney |
| 1,810,466 A | 6/1931 | Deutsch |

(Continued)

FOREIGN PATENT DOCUMENTS

| DE | 37 39 532 | 12/1988 |
| DE | 37 37 121 | 5/1989 |

(Continued)

OTHER PUBLICATIONS

Kagaya, "Laparoscopic cholecystectomy via two ports, using the 'Twin-Port' system", J. Hepatobiliary Pancreat Surg (2001) 8:76-80.

*Primary Examiner* — Christian Sevilla
(74) *Attorney, Agent, or Firm* — Bookoff McAndrews, PLLC

(57) ABSTRACT

A wound retractor (320) comprises a distal ring (3) for insertion through a wound opening (6), a proximal ring (4) for location externally of the wound opening (6), a valve (10) mounted to the proximal ring (4), and a sleeve (2) for retracting laterally the sides of the wound opening (6). The wound retractor (320) also comprises a flexible release member (81) for releasing the distal ring (3) from a retracting configuration for removal of the distal ring (3) from the wound opening (6). A first end (301) of the release member (81) is attached to the valve housing (102), the release member (81) loops around the distal ring (3), and a second end (302) of the release member (81) is movable relative to the proximal ring (4) to release the distal ring (3) from the retracting configuration.

18 Claims, 14 Drawing Sheets

(56) References Cited

U.S. PATENT DOCUMENTS

| | | |
|---|---|---|
| 2,219,564 A | 10/1940 | Reyniers |
| 2,305,289 A | 12/1942 | Coburg |
| 2,695,608 A | 11/1954 | Gibbon |
| 2,835,253 A | 5/1958 | Borgeson |
| 2,853,075 A | 10/1958 | Hoffman |
| 3,039,468 A | 6/1962 | Price |
| 3,111,943 A | 11/1963 | Orndorff |
| 3,244,169 A | 4/1966 | Baxter |
| 3,253,594 A | 5/1966 | Matthews et al. |
| 3,304,671 A | 2/1967 | Kintish et al. |
| 3,313,299 A | 4/1967 | Spademan |
| 3,329,390 A | 7/1967 | Hulsey |
| 3,332,417 A | 7/1967 | Blanford et al. |
| 3,347,226 A | 10/1967 | Harrower |
| 3,347,227 A | 10/1967 | Harrower |
| 3,397,692 A | 8/1968 | Creager, Jr. et al. |
| 3,402,710 A | 9/1968 | Paleschuck |
| 3,447,533 A | 6/1969 | Spicer |
| 3,522,800 A | 8/1970 | Lesser |
| 3,523,534 A | 8/1970 | Nolan |
| 3,570,475 A | 3/1971 | Weinstein |
| 3,592,198 A | 7/1971 | Evans |
| 3,656,485 A | 4/1972 | Robertson |
| 3,685,786 A | 8/1972 | Woodson |
| 3,717,151 A | 2/1973 | Collett |
| 3,729,006 A | 4/1973 | Wilder et al. |
| 3,782,370 A | 1/1974 | McDonald |
| 3,797,478 A | 3/1974 | Walsh et al. |
| 3,807,393 A | 4/1974 | McDonald |
| 3,828,764 A | 8/1974 | Jones |
| 3,841,332 A | 10/1974 | Treacle |
| 3,853,126 A | 12/1974 | Schulte |
| 3,853,127 A | 12/1974 | Spademan |
| 3,856,021 A | 12/1974 | Macintosh |
| 3,907,389 A | 9/1975 | Cox et al. |
| 3,915,171 A | 10/1975 | Shermeta |
| 3,965,890 A | 6/1976 | Gauthier |
| 3,996,623 A | 12/1976 | Kaster |
| 3,998,217 A | 12/1976 | Trumbull et al. |
| 4,000,739 A | 1/1977 | Stevens |
| 4,016,884 A | 4/1977 | Kwan-Gett |
| 4,024,872 A | 5/1977 | Muldoon |
| 4,030,500 A | 6/1977 | Ronnquist |
| 4,083,370 A | 4/1978 | Taylor |
| 4,096,853 A | 6/1978 | Weigand |
| 4,130,113 A | 12/1978 | Graham |
| 4,177,814 A | 12/1979 | Knepshield |
| 4,188,945 A | 2/1980 | Wenander |
| 4,217,664 A | 8/1980 | Faso |
| 4,228,792 A | 10/1980 | Rhys-Davies |
| 4,239,036 A | 12/1980 | Krieger |
| 4,240,411 A | 12/1980 | Hosono |
| 4,253,201 A | 3/1981 | Ross et al. |
| 4,306,562 A | 12/1981 | Osborne |
| 4,321,915 A | 3/1982 | Leighton |
| 4,331,138 A | 5/1982 | Jessen |
| 4,338,934 A | 7/1982 | Spademan |
| 4,338,937 A | 7/1982 | Lehrman |
| 4,367,728 A | 1/1983 | Mutke |
| 4,399,816 A | 8/1983 | Spangler |
| 4,411,659 A | 10/1983 | Jensen et al. |
| 4,421,296 A | 12/1983 | Stephens |
| 4,424,833 A | 1/1984 | Spector |
| 4,428,364 A | 1/1984 | Bartolo |
| 4,430,081 A | 2/1984 | Timmermans |
| 4,434,791 A | 3/1984 | Darnell |
| 4,436,519 A | 3/1984 | O'Neill |
| 4,485,490 A | 12/1984 | Akers et al. |
| 4,488,877 A | 12/1984 | Klein |
| 4,543,088 A | 9/1985 | Bootman et al. |
| 4,550,713 A | 11/1985 | Hyman |
| 4,553,537 A | 11/1985 | Rosenberg |
| 4,601,710 A | 7/1986 | Moll |
| 4,610,665 A | 9/1986 | Matsumoto |
| 4,626,245 A | 12/1986 | Weinstein |
| 4,634,424 A | 1/1987 | O'Boyle |
| 4,649,904 A | 3/1987 | Krauter |
| 4,654,030 A | 3/1987 | Moll et al. |
| 4,673,393 A | 6/1987 | Suzuki et al. |
| 4,673,394 A | 6/1987 | Fenton |
| 4,755,170 A | 7/1988 | Golden |
| 4,776,843 A | 10/1988 | Martinez et al. |
| 4,777,943 A | 10/1988 | Chvapil |
| 4,784,646 A | 11/1988 | Feingold |
| 4,798,594 A | 1/1989 | Hillstead |
| 4,809,679 A | 3/1989 | Shimonaka |
| 4,863,438 A | 9/1989 | Gauderer |
| 4,889,107 A | 12/1989 | Kaufman |
| 4,895,565 A | 1/1990 | Hillstead |
| 4,897,081 A | 1/1990 | Poirier |
| 4,903,710 A | 2/1990 | Jessamine et al. |
| 4,950,222 A | 8/1990 | Scott et al. |
| 4,950,223 A | 8/1990 | Silvanov |
| 4,984,564 A | 1/1991 | Yuen |
| 4,991,593 A | 2/1991 | LeVahn |
| 4,998,538 A | 3/1991 | Charowsky et al. |
| 5,015,228 A | 5/1991 | Columbus et al. |
| 5,019,101 A | 5/1991 | Purkait |
| 5,026,366 A | 6/1991 | Leckrone |
| 5,041,095 A | 8/1991 | Littrell |
| 5,045,070 A | 9/1991 | Grodecki et al. |
| D320,658 S | 10/1991 | Quigley et al. |
| 5,071,411 A | 12/1991 | Hillstead |
| 5,074,878 A | 12/1991 | Bark et al. |
| 5,082,005 A | 1/1992 | Kaldany |
| 5,086,763 A | 2/1992 | Hathman |
| 5,092,846 A | 3/1992 | Nishijima |
| 5,125,897 A | 6/1992 | Quinn et al. |
| 5,141,498 A | 8/1992 | Christian |
| 5,149,327 A | 9/1992 | Oshiyama |
| 5,156,617 A | 10/1992 | Reid |
| 5,158,553 A | 10/1992 | Berry et al. |
| 5,159,921 A | 11/1992 | Hoover |
| 5,161,773 A | 11/1992 | Tower |
| 5,167,636 A | 12/1992 | Clement |
| 5,178,162 A | 1/1993 | Bose |
| 5,188,595 A | 2/1993 | Jacobi |
| 5,192,301 A | 3/1993 | Kamiya et al. |
| 5,207,656 A | 5/1993 | Kranys |
| 5,209,737 A | 5/1993 | Richartt |
| 5,211,370 A | 5/1993 | Powers |
| 5,211,633 A | 5/1993 | Strouder |
| 5,213,114 A | 5/1993 | Bailey, Jr. |
| 5,234,455 A | 8/1993 | Mulhollan |
| 5,242,409 A | 9/1993 | Buelna |
| 5,248,304 A | 9/1993 | Vigdorchik et al. |
| 5,261,883 A | 11/1993 | Hood et al. |
| 5,263,922 A | 11/1993 | Sova et al. |
| 5,269,763 A | 12/1993 | Boehmer |
| 5,269,772 A | 12/1993 | Wilk |
| D343,236 S | 1/1994 | Quigley et al. |
| 5,279,575 A | 1/1994 | Sugarbaker |
| D346,022 S | 4/1994 | Quigley et al. |
| 5,299,582 A | 4/1994 | Potts |
| 5,300,036 A | 4/1994 | Mueller |
| 5,308,336 A | 5/1994 | Hart et al. |
| 5,309,896 A | 5/1994 | Moll et al. |
| 5,316,541 A | 5/1994 | Fischer |
| 5,320,611 A | 6/1994 | Bonutti |
| 5,330,437 A | 7/1994 | Durman |
| 5,330,497 A | 7/1994 | Freitas |
| 5,334,143 A | 8/1994 | Carroll |
| 5,336,192 A | 8/1994 | Palestrant |
| 5,342,315 A | 8/1994 | Rowe et al. |
| 5,342,385 A | 8/1994 | Norelli et al. |
| 5,350,364 A | 9/1994 | Stephens et al. |
| 5,364,345 A | 11/1994 | Lowery et al. |
| 5,366,478 A | 11/1994 | Brinkerhoff et al. |
| 5,368,545 A | 11/1994 | Schaller et al. |
| 5,383,861 A | 1/1995 | Hempel |
| 5,385,553 A | 1/1995 | Hart et al. |
| 5,391,153 A | 2/1995 | Haber et al. |
| 5,391,156 A | 2/1995 | Hildwein et al. |
| 5,395,367 A | 3/1995 | Wilk |

(56) References Cited

U.S. PATENT DOCUMENTS

| | | |
|---|---|---|
| 5,403,264 A | 4/1995 | Wohlers |
| 5,407,433 A | 4/1995 | Loomas |
| 5,423,848 A | 6/1995 | Washizuka et al. |
| 5,429,609 A | 7/1995 | Yoon |
| 5,431,676 A | 7/1995 | Durbal |
| 5,443,452 A | 8/1995 | Hart et al. |
| 5,456,284 A | 10/1995 | Ryan |
| 5,476,475 A | 12/1995 | Gadberry |
| 5,480,410 A * | 1/1996 | Cuschieri et al. ............ 606/213 |
| 5,496,280 A | 3/1996 | Vandenbroeck |
| 5,503,112 A | 4/1996 | Luhman |
| 5,514,109 A | 5/1996 | Mollenauer et al. |
| 5,514,133 A | 5/1996 | Golub et al. |
| 5,520,632 A | 5/1996 | Leveen |
| 5,522,791 A | 6/1996 | Leyva |
| 5,522,824 A | 6/1996 | Ashby |
| 5,524,644 A | 6/1996 | Crook |
| 5,526,536 A | 6/1996 | Cartmill |
| 5,545,179 A | 8/1996 | Williamson, IV |
| 5,562,632 A | 10/1996 | Davila |
| 5,562,688 A | 10/1996 | Riza |
| 5,577,993 A | 11/1996 | Zhu et al. |
| 5,584,850 A | 12/1996 | Hart et al. |
| 5,601,579 A | 2/1997 | Semertzides |
| 5,620,415 A | 4/1997 | Lucey |
| 5,632,979 A | 5/1997 | Goldberg |
| 5,634,911 A | 6/1997 | Hermann et al. |
| 5,634,936 A | 6/1997 | Linden |
| 5,634,937 A | 6/1997 | Mollenauer et al. |
| 5,636,645 A | 6/1997 | Ou |
| 5,640,977 A | 6/1997 | Leahy et al. |
| 5,649,550 A | 7/1997 | Crook |
| 5,653,705 A | 8/1997 | de la Torre et al. |
| 5,657,963 A | 8/1997 | Hinchliffe |
| 5,658,272 A | 8/1997 | Hasson |
| 5,658,306 A | 8/1997 | Kieturakis |
| 5,672,168 A | 9/1997 | de la Torre et al. |
| 5,685,854 A | 11/1997 | Green |
| 5,707,703 A | 1/1998 | Rothrum et al. |
| 5,709,664 A | 1/1998 | Vandenbroeck |
| 5,720,730 A | 2/1998 | Blake, III |
| 5,738,628 A | 4/1998 | Sierocuk et al. |
| 5,741,234 A | 4/1998 | Aboul-Hosn |
| 5,741,298 A | 4/1998 | MacLeod |
| 5,749,882 A | 5/1998 | Hart et al. |
| 5,755,660 A | 5/1998 | Tyagi |
| 5,769,783 A | 6/1998 | Fowler |
| 5,782,812 A | 7/1998 | Hart et al. |
| 5,795,290 A | 8/1998 | Bridges |
| 5,803,919 A | 9/1998 | Hart et al. |
| 5,803,921 A | 9/1998 | Bonadio |
| 5,807,350 A | 9/1998 | Diaz |
| 5,810,721 A | 9/1998 | Mueller et al. |
| 5,813,409 A | 9/1998 | Leahy et al. |
| 5,814,026 A | 9/1998 | Yoon |
| 5,817,062 A | 10/1998 | Flom |
| 5,820,555 A | 10/1998 | Watkins, III et al. |
| 5,832,925 A | 11/1998 | Rothrum |
| 5,853,395 A * | 12/1998 | Crook et al. ............... 604/174 |
| 5,865,728 A | 2/1999 | Moll et al. |
| 5,871,474 A | 2/1999 | Hermann et al. |
| 5,882,344 A | 3/1999 | Strouder |
| 5,899,208 A | 5/1999 | Bonadio |
| 5,904,703 A | 5/1999 | Gilson |
| 5,906,577 A | 5/1999 | Beane et al. |
| 5,916,232 A | 6/1999 | Hart |
| 5,947,922 A | 9/1999 | MacLeod |
| 5,951,467 A | 9/1999 | Picha et al. |
| 5,957,913 A | 9/1999 | de la Torre et al. |
| 5,964,781 A | 10/1999 | Mollenauer et al. |
| 5,993,485 A | 11/1999 | Beckers |
| 5,994,450 A | 11/1999 | Pearce |
| 5,997,515 A | 12/1999 | de la Torre et al. |
| 6,024,736 A | 2/2000 | de la Torre et al. |
| 6,025,067 A | 2/2000 | Fay |
| 6,033,426 A | 3/2000 | Kaji |
| 6,033,428 A | 3/2000 | Sardella |
| 6,042,573 A | 3/2000 | Lucey |
| 6,048,309 A | 4/2000 | Flom et al. |
| 6,059,816 A | 5/2000 | Moenning |
| 6,077,288 A | 6/2000 | Shimomura et al. |
| 6,099,506 A | 8/2000 | Macoviak et al. |
| 6,110,154 A | 8/2000 | Shimomura et al. |
| 6,123,689 A | 9/2000 | To |
| 6,142,935 A | 11/2000 | Flom et al. |
| 6,142,936 A | 11/2000 | Beane et al. |
| 6,150,608 A | 11/2000 | Wambeke |
| 6,159,182 A | 12/2000 | Davis |
| 6,162,172 A | 12/2000 | Cosgrove et al. |
| 6,162,196 A | 12/2000 | Hart et al. |
| 6,162,206 A | 12/2000 | Bindokas |
| 6,163,949 A | 12/2000 | Neuenschwander |
| 6,164,279 A | 12/2000 | Tweedle |
| 6,171,282 B1 | 1/2001 | Ragsdale |
| 6,183,486 B1 | 2/2001 | Snow et al. |
| 6,238,373 B1 | 5/2001 | de la Torre et al. |
| 6,254,533 B1 | 7/2001 | Fadem et al. |
| 6,254,534 B1 | 7/2001 | Butler et al. |
| 6,258,065 B1 | 7/2001 | Dennis |
| 6,315,770 B1 | 11/2001 | de la Torre et al. |
| 6,319,246 B1 | 11/2001 | de la Torre et al. |
| 6,322,541 B2 | 11/2001 | West |
| 6,346,074 B1 | 2/2002 | Roth |
| 6,382,211 B1 | 5/2002 | Crook |
| 6,420,475 B1 | 7/2002 | Chen |
| 6,440,063 B1 | 8/2002 | Beane |
| 6,450,983 B1 | 9/2002 | Rambo |
| 6,454,783 B1 | 9/2002 | Piskun |
| 6,464,686 B1 | 10/2002 | O'Hara et al. |
| 6,485,435 B1 | 11/2002 | Bakal |
| 6,488,620 B1 | 12/2002 | Segermark et al. |
| 6,533,734 B1 | 3/2003 | Corley, III et al. |
| 6,551,270 B1 | 4/2003 | Bimbo et al. |
| 6,554,793 B1 | 4/2003 | Pauker |
| 6,578,577 B2 | 6/2003 | Bonadio et al. |
| 6,582,364 B2 | 6/2003 | Butler et al. |
| 6,589,167 B1 | 7/2003 | Shimonmura et al. |
| 6,589,211 B1 | 7/2003 | MacLeod |
| 6,607,504 B2 | 8/2003 | Haarala |
| 6,613,952 B2 | 9/2003 | Rambo |
| 6,623,426 B2 | 9/2003 | Bonadio et al. |
| 6,706,050 B1 | 3/2004 | Giannadakis |
| 6,714,298 B2 | 3/2004 | Ryer |
| 6,723,044 B2 | 4/2004 | Pulford |
| 6,796,940 B2 | 9/2004 | Bonadio et al. |
| 6,797,765 B2 | 9/2004 | Pearce |
| 6,814,078 B2 | 11/2004 | Crook |
| 6,814,700 B1 | 11/2004 | Mueller et al. |
| 6,840,951 B2 | 1/2005 | de la Torre et al. |
| 6,846,287 B2 | 1/2005 | Bonadio et al. |
| 6,860,463 B2 | 3/2005 | Hartley |
| 6,866,861 B1 | 3/2005 | Luhman |
| 6,884,253 B1 | 4/2005 | McFarlane |
| 6,902,541 B2 | 6/2005 | McNally et al. |
| 6,908,430 B2 | 6/2005 | Caldwell |
| 6,916,331 B2 | 7/2005 | Mollenauer et al. |
| 6,936,037 B2 | 8/2005 | Bubb |
| 6,939,296 B2 | 9/2005 | Ewers |
| 6,945,932 B1 | 9/2005 | Caldwell et al. |
| 6,958,037 B2 | 10/2005 | Ewers |
| 6,979,324 B2 | 12/2005 | Bybordi |
| 7,008,377 B2 | 3/2006 | Beane |
| 7,052,454 B2 | 5/2006 | Taylor |
| 7,081,089 B2 | 7/2006 | Bonadio et al. |
| 7,118,528 B1 | 10/2006 | Piskun |
| 7,195,590 B2 | 3/2007 | Butler et al. |
| 7,297,106 B2 | 11/2007 | Yamada et al. |
| 7,300,399 B2 | 11/2007 | Bonadio et al. |
| 7,344,547 B2 | 3/2008 | Piskun |
| 7,445,597 B2 | 11/2008 | Butler et al. |
| 7,537,564 B2 | 5/2009 | Bonadio et al. |
| 7,540,839 B2 | 6/2009 | Butler et al. |
| 2001/0037053 A1 | 11/2001 | Bonadio et al. |
| 2001/0039430 A1 | 11/2001 | Dubrul et al. |

(56) References Cited

U.S. PATENT DOCUMENTS

| | | |
|---|---|---|
| 2001/0047188 A1 | 11/2001 | Bonadio et al. |
| 2002/0002324 A1 | 1/2002 | Mcmanus |
| 2002/0010389 A1 | 1/2002 | Butler et al. |
| 2002/0038077 A1 | 3/2002 | de la Torre et al. |
| 2002/0072762 A1 | 6/2002 | Bonadio et al. |
| 2002/0111536 A1 | 8/2002 | Cuschieri et al. |
| 2003/0028179 A1 | 2/2003 | Piskun |
| 2003/0078478 A1 | 4/2003 | Bonadio et al. |
| 2003/0139756 A1 | 7/2003 | Brustad |
| 2003/0187376 A1 | 10/2003 | Rambo |
| 2003/0192553 A1 | 10/2003 | Rambo |
| 2003/0225392 A1 | 12/2003 | McMichael |
| 2003/0236549 A1 | 12/2003 | Bonadio et al. |
| 2004/0015185 A1 | 1/2004 | Ewers et al. |
| 2004/0024363 A1 | 2/2004 | Goldberg |
| 2004/0049100 A1 | 3/2004 | Butler |
| 2004/0073090 A1 | 4/2004 | Butler |
| 2004/0092795 A1 | 5/2004 | Bonadio et al. |
| 2004/0092796 A1 | 5/2004 | Butler et al. |
| 2004/0093018 A1 | 5/2004 | Johnson |
| 2004/0097793 A1 | 5/2004 | Butler et al. |
| 2004/0106942 A1 | 6/2004 | Taylor |
| 2004/0143158 A1 | 7/2004 | Hart et al. |
| 2004/0154624 A1* | 8/2004 | Bonadio et al. ............... 128/849 |
| 2004/0215063 A1 | 10/2004 | Bonadio et al. |
| 2004/0249248 A1 | 12/2004 | Bonadio et al. |
| 2005/0020884 A1 | 1/2005 | Hart et al. |
| 2005/0033246 A1 | 2/2005 | Ahlberg |
| 2005/0059865 A1 | 3/2005 | Kahle |
| 2005/0065543 A1 | 3/2005 | Kahle et al. |
| 2005/0090713 A1 | 4/2005 | Gozales |
| 2005/0090716 A1 | 4/2005 | Bonadio et al. |
| 2005/0090717 A1 | 4/2005 | Bonadio et al. |
| 2005/0131349 A1 | 6/2005 | Albrecht |
| 2005/0148823 A1 | 7/2005 | Vaugh et al. |
| 2005/0155611 A1 | 7/2005 | Vaugh et al. |
| 2005/0159647 A1 | 7/2005 | Hart et al. |
| 2005/0192483 A1 | 9/2005 | Bonadio et al. |
| 2005/0192598 A1 | 9/2005 | Johnson |
| 2005/0197537 A1 | 9/2005 | Bonadio et al. |
| 2005/0203346 A1 | 9/2005 | Bonadio et al. |
| 2005/0209510 A1 | 9/2005 | Bonadio et al. |
| 2005/0240082 A1 | 10/2005 | Bonadio et al. |
| 2005/0241647 A1 | 11/2005 | Nguyen |
| 2005/0277946 A1 | 12/2005 | Greenhalgh |
| 2005/0288558 A1 | 12/2005 | Ewers |
| 2005/0288634 A1 | 12/2005 | O'Herron |
| 2006/0020164 A1 | 1/2006 | Butler et al. |
| 2006/0020241 A1 | 1/2006 | Piskun et al. |
| 2006/0041270 A1 | 2/2006 | Lenker |
| 2006/0047284 A1 | 3/2006 | Gresham |
| 2006/0106402 A1 | 5/2006 | McLucas |
| 2006/0149306 A1 | 7/2006 | Hart et al. |
| 2006/0161050 A1 | 7/2006 | Butler et al. |
| 2006/0247498 A1 | 11/2006 | Bonadio et al. |
| 2006/0247499 A1 | 11/2006 | Butler et al. |
| 2006/0247500 A1 | 11/2006 | Voegele et al. |
| 2006/0264706 A1 | 11/2006 | Piskun |
| 2007/0004968 A1 | 1/2007 | Bonadio et al. |
| 2007/0049966 A1 | 3/2007 | Bonadio et al. |
| 2007/0093695 A1 | 4/2007 | Bonadio et al. |
| 2007/0118175 A1 | 5/2007 | Butler et al. |
| 2007/0203398 A1 | 8/2007 | Bonadio et al. |
| 2007/0255219 A1 | 11/2007 | Vaugh et al. |
| 2008/0027476 A1 | 1/2008 | Piskun |
| 2008/0097162 A1 | 4/2008 | Bonadio et al. |
| 2008/0097163 A1 | 4/2008 | Butler et al. |
| 2008/0255519 A1 | 10/2008 | Piskun et al. |
| 2008/0281161 A1 | 11/2008 | Albrecht et al. |
| 2008/0281162 A1 | 11/2008 | Albrecht et al. |
| 2009/0036745 A1 | 2/2009 | Bonadio et al. |
| 2009/0069837 A1 | 3/2009 | Bonadio et al. |
| 2009/0187079 A1 | 7/2009 | Albrecht et al. |

FOREIGN PATENT DOCUMENTS

| | | |
|---|---|---|
| EP | 0113520 | 7/1984 |
| EP | 0142262 | 5/1985 |
| EP | 0537768 | 4/1993 |
| EP | 0950376 | 10/1999 |
| EP | 1118657 | 7/2001 |
| GB | 1151993 | 5/1969 |
| GB | 1355611 | 6/1974 |
| GB | 1372491 | 10/1974 |
| GB | 1379772 | 1/1975 |
| GB | 1400808 | 7/1975 |
| GB | 1407023 | 9/1975 |
| GB | 1496696 | 12/1977 |
| GB | 2071502 | 9/1981 |
| GB | 2255019 | 10/1992 |
| GB | 2275420 | 8/1994 |
| JP | 10-108868 | 4/1998 |
| JP | 11-290327 | 10/1999 |
| JP | 2001-61850 | 3/2001 |
| JP | 2002-28163 | 1/2002 |
| JP | 2004-195037 | 7/2004 |
| RU | 1342485 | 1/1997 |
| WO | WO 86/06272 | 11/1986 |
| WO | WO 92/11880 | 7/1992 |
| WO | WO 92/21292 | 12/1992 |
| WO | WO 93/05740 | 4/1993 |
| WO | WO 95/05207 | 2/1995 |
| WO | WO 95/07056 | 3/1995 |
| WO | WO 95/22289 | 8/1995 |
| WO | WO 95/24864 | 9/1995 |
| WO | WO 95/27445 | 10/1995 |
| WO | WO 95/27468 | 10/1995 |
| WO | WO 96/36283 | 11/1996 |
| WO | WO 97/32514 | 9/1997 |
| WO | WO 97/32515 | 9/1997 |
| WO | WO 98/35614 | 8/1998 |
| WO | WO 98/48724 | 11/1998 |
| WO | WO 99/03416 | 1/1999 |
| WO | WO 99/25268 | 5/1999 |
| WO | WO 99/29250 | 6/1999 |
| WO | WO 00/32116 | 6/2000 |
| WO | WO 00/32117 | 6/2000 |
| WO | WO 00/32119 | 6/2000 |
| WO | WO 00/32120 | 6/2000 |
| WO | WO 00/35356 | 6/2000 |
| WO | WO 00/54675 | 9/2000 |
| WO | WO 00/54676 | 9/2000 |
| WO | WO 00/54677 | 9/2000 |
| WO | WO 01/08563 | 2/2001 |
| WO | WO 01/08581 | 2/2001 |
| WO | WO 01/26558 | 4/2001 |
| WO | WO 01/91652 | 12/2001 |
| WO | WO 02/17800 A2 | 3/2002 |
| WO | WO 02/34108 A2 | 5/2002 |
| WO | WO 03/026512 A1 | 4/2003 |
| WO | WO 03/034908 A3 | 5/2003 |
| WO | WO 03/061480 A1 | 7/2003 |
| WO | WO 03/103548 A1 | 12/2003 |
| WO | WO 2004/026153 A1 | 4/2004 |
| WO | WO 2004/030547 A1 | 4/2004 |
| WO | WO 2005/009257 A2 | 2/2005 |
| WO | WO 2005/034766 A2 | 4/2005 |
| WO | WO 2006/040748 A1 | 4/2006 |

* cited by examiner

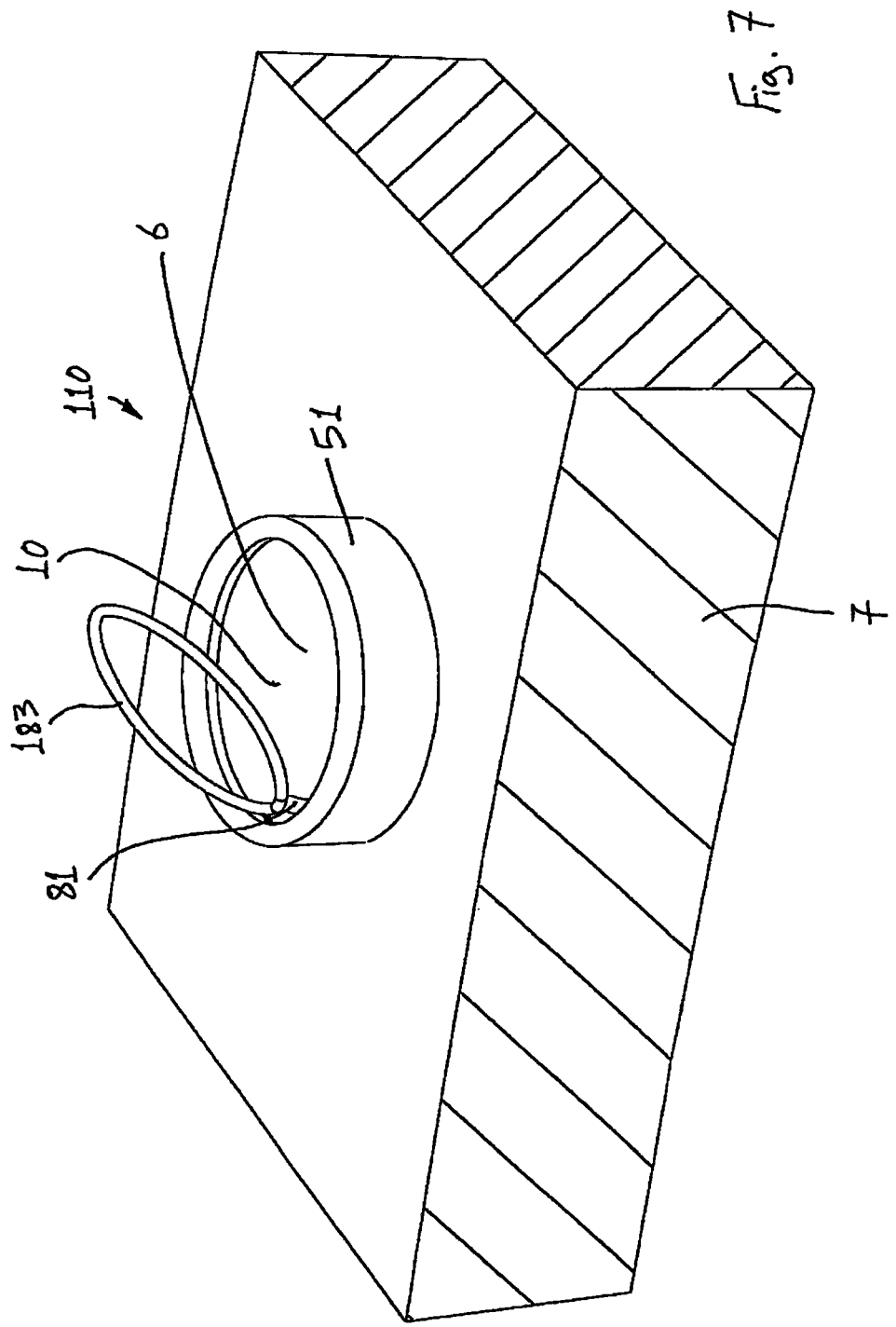

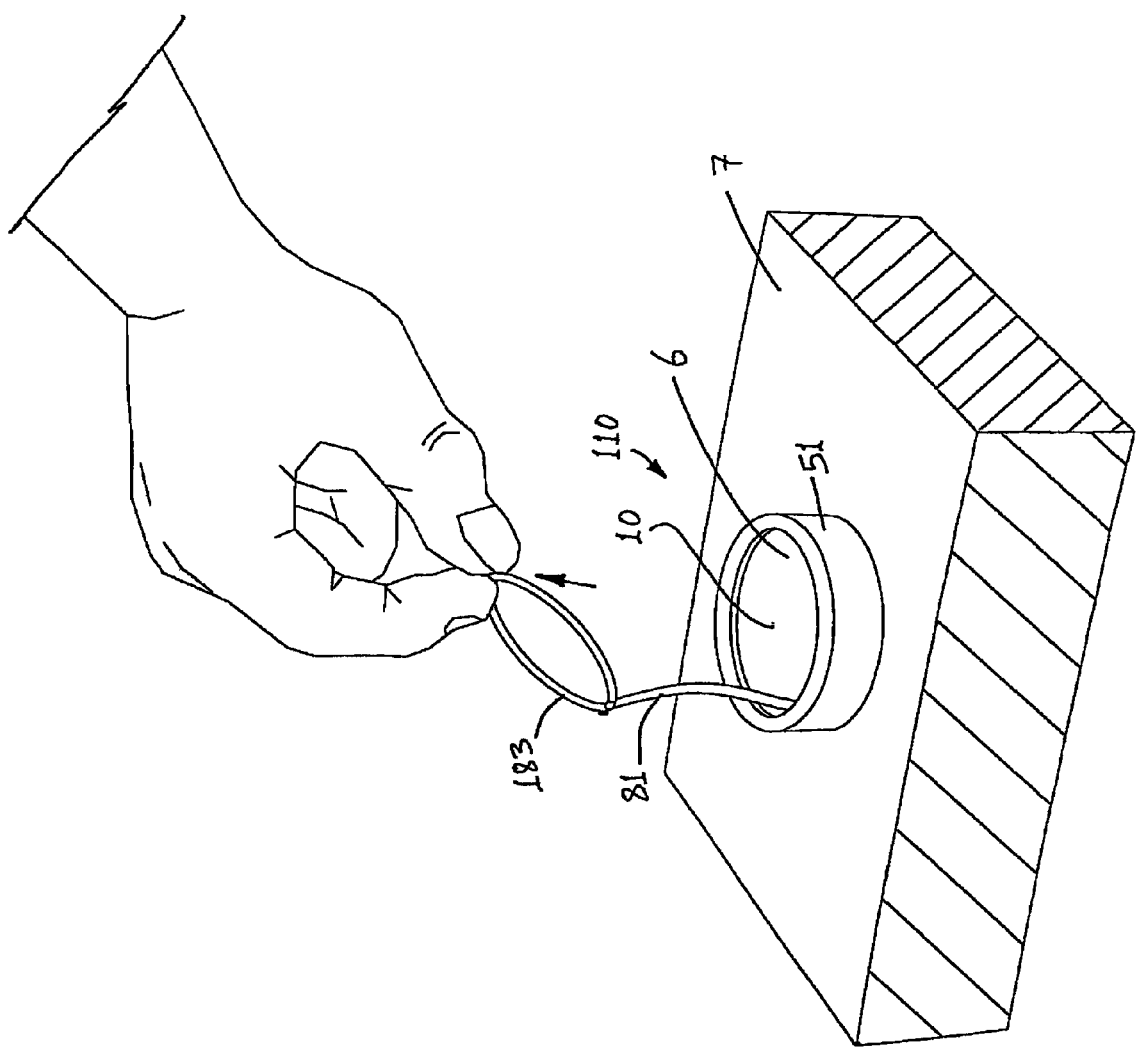

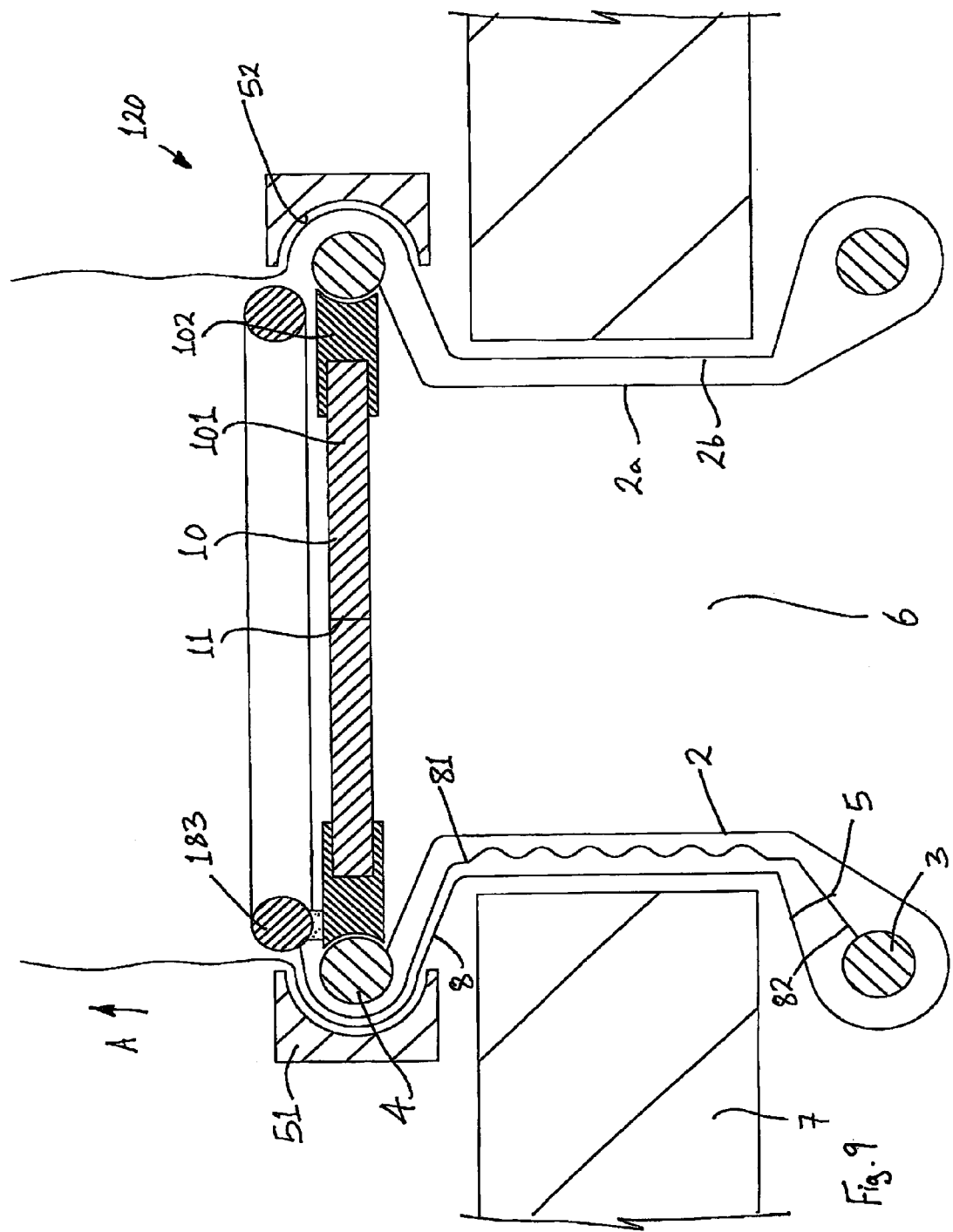

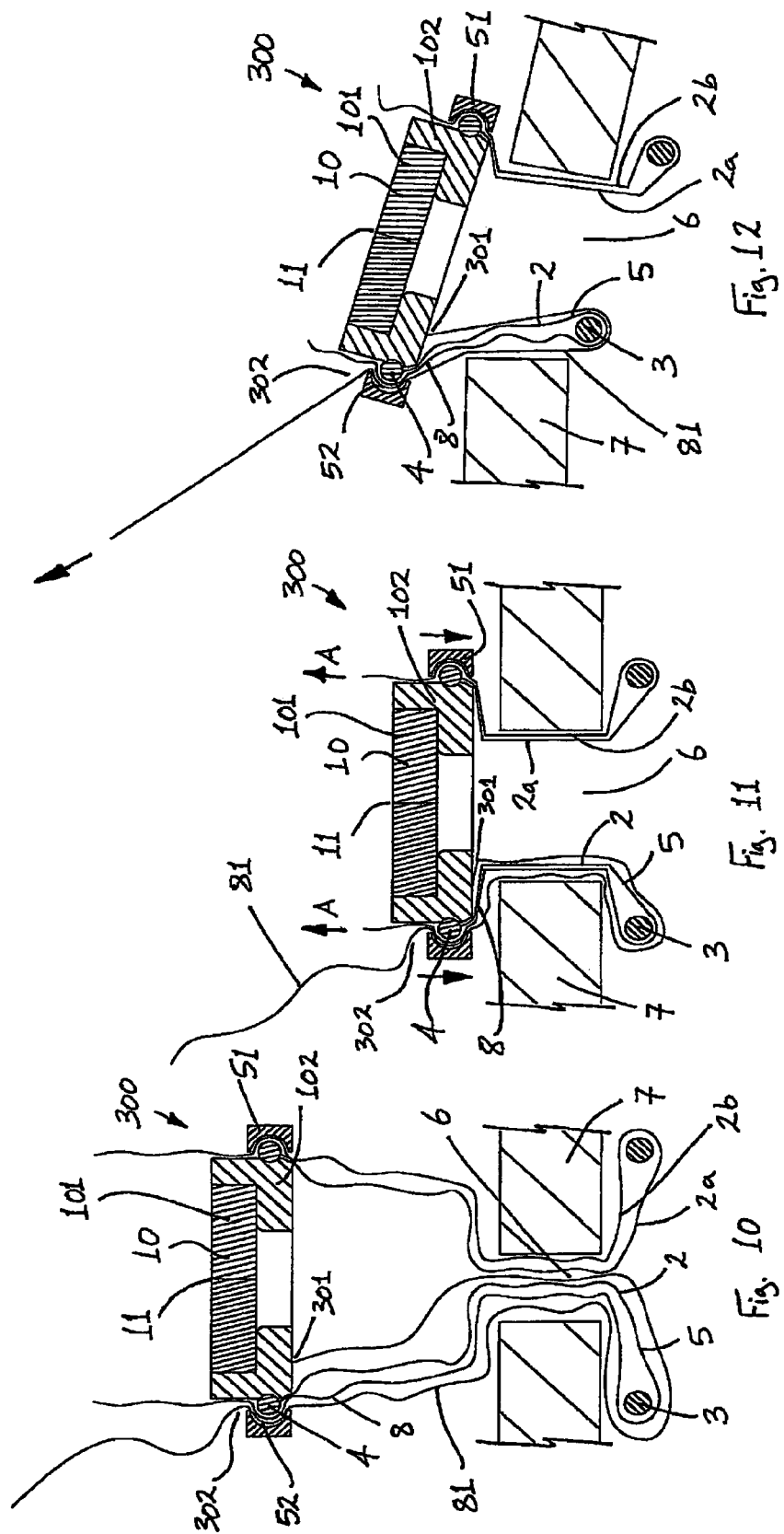

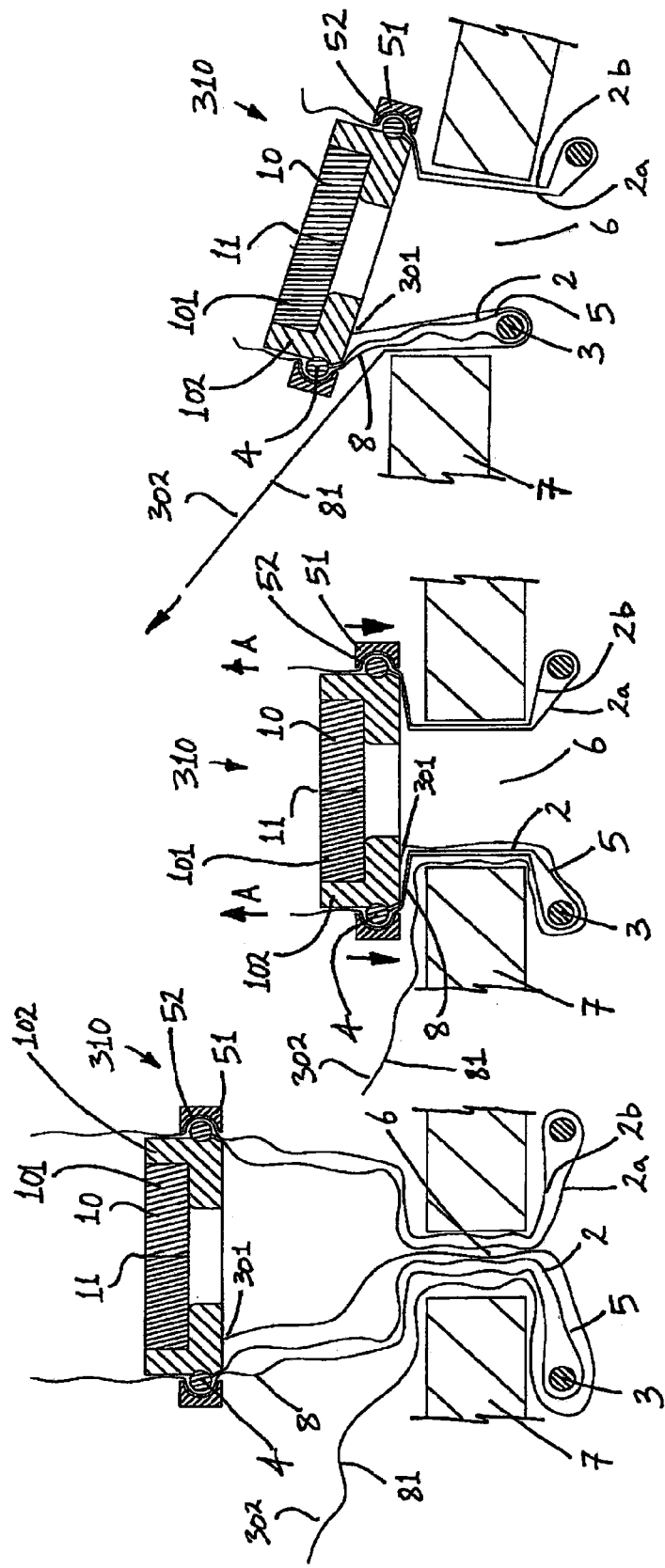

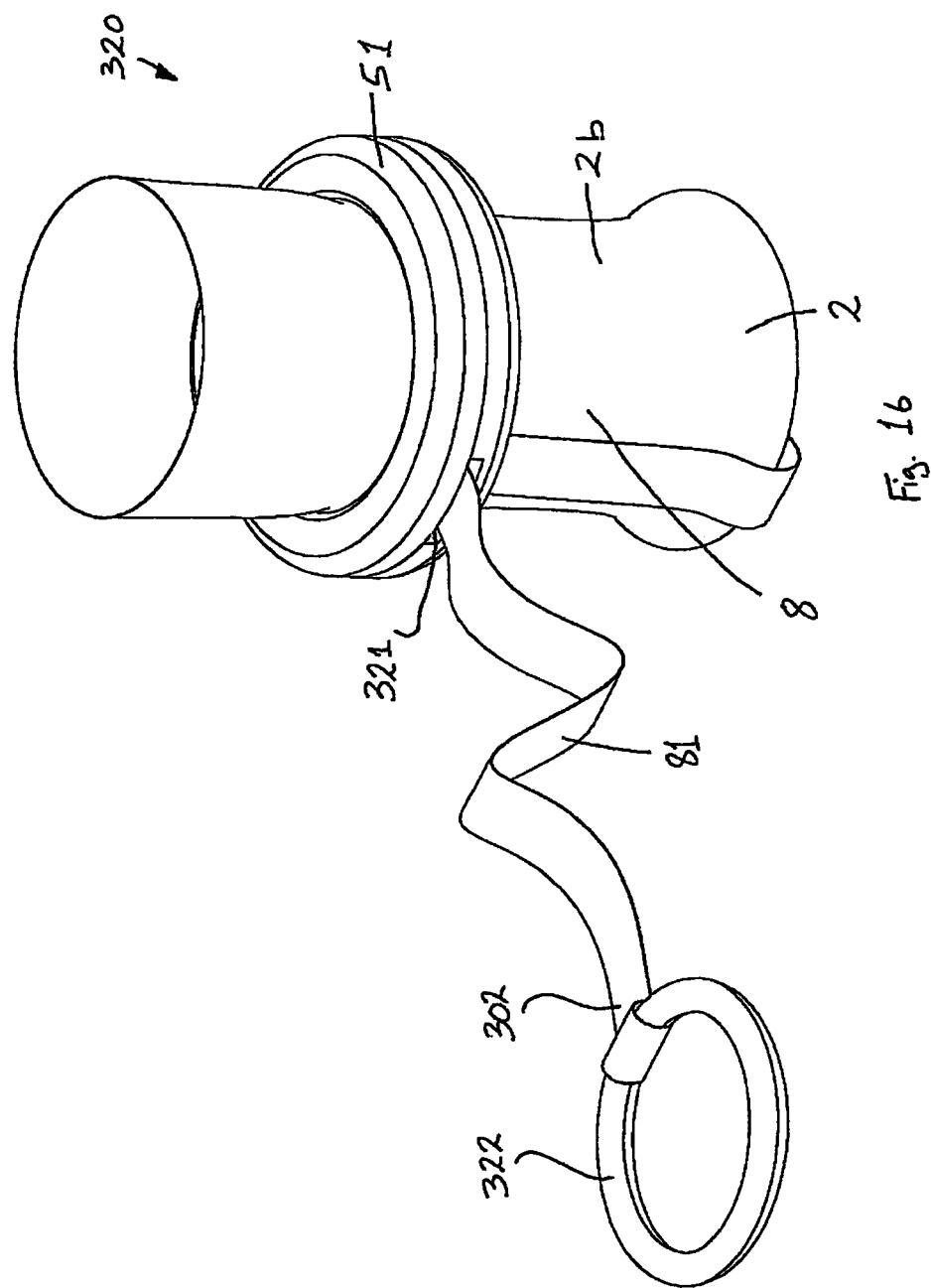

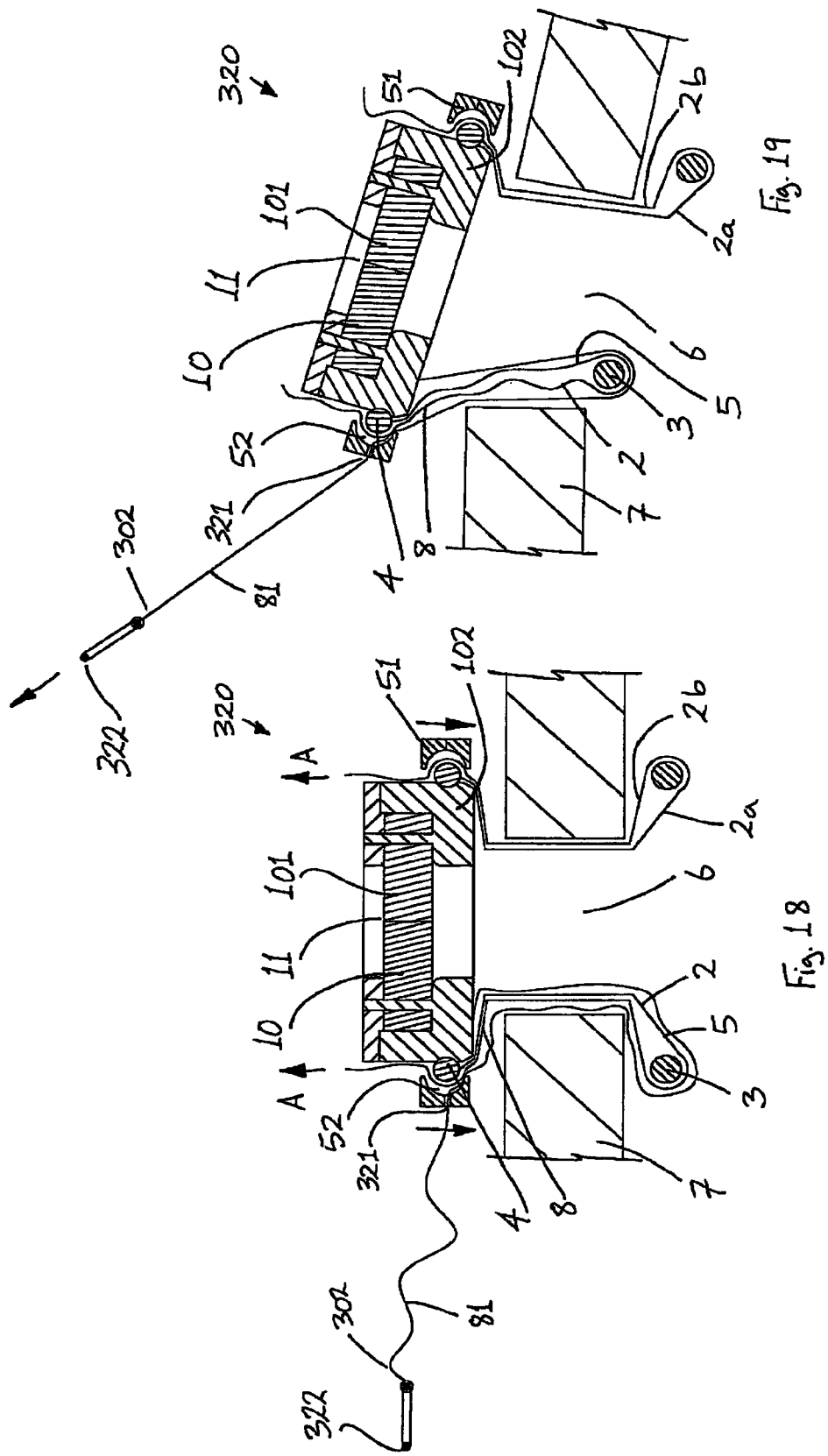

WOUND RETRACTOR

This application is a Continuation of application Ser. No. 11/486,383, filed Jul. 14, 2006 now U.S. Pat. No. 8,021,296, which is a Continuation-In-Part of U.S. application Ser. No. 10/678,653, filed Oct. 6, 2003 now U.S. Pat. No. 7,559,893, which claims the benefit of U.S. Provisional Application Nos. 60/415,780, filed on Oct. 4, 2002; 60/428,215, filed on Nov. 22, 2002; and 60/490,909, filed on Jul. 30, 2003.

U.S. application Ser. No. 11/486,383 claims the benefit of U.S. Provisional Application Nos. 60/699,371 filed on Jul. 15, 2005, and 60/724,785 filed on Oct. 11, 2005.

INTRODUCTION

This invention relates to a wound retractor. In particular this invention relates to a wound retractor for retracting laterally the sides of a wound opening to provide maximum exposure of an organ or body structures for examination and/or access for surgical procedures.

Some conventional wound retractors are difficult and cumbersome to use, and/or are relatively expensive. In addition, some conventional wound retractors are limited to use with a particular size of incision and a particular patient anatomy.

This invention is directed towards providing an improved wound retractor which will address at least some of these problems.

STATEMENTS OF INVENTION

According to the invention there is provided a wound retractor comprising:—
- a distal member for insertion through a wound opening;
- a proximal member for location externally of the wound opening;
- a connecting member extending at least between the distal member and the proximal member to retract laterally the sides of the wound opening; and
- a release member for releasing the distal member from a retracting configuration for removal of the distal member from the wound opening;
- the release member being configured to extend in two layers through the wound opening.

In the retracting configuration, the distal member is securely held in place in the retracted wound opening. By releasing the distal member from the retracting configuration, it is then possible to remove the distal member from the wound opening.

In one embodiment of the invention the release member extends in two layers between the distal member and the proximal member.

In another embodiment the retractor comprises a valve. The valve maintains gas pressure within the interior of the wound opening even when the wound opening is retracted. The valve may be mounted to the proximal member. The valve may be at least partially of a gelatinous elastomeric material. The valve may comprise a gelatinous elastomeric material portion and a housing portion. The housing portion may be mounted to the proximal member. The valve may comprise an opening extending therethrough. The opening through the valve facilitates access for instruments to pass through the valve and the retracted wound opening to access the interior of the wound opening. The opening may be biased towards a closed configuration. The opening is biased towards the closed configuration to minimise loss of gas pressure upon exchange of instruments through the opening. The opening may comprise a pinhole. The valve may be an instrument seal.

In another embodiment the release member is looped around the distal member. A first end of the release member may be attached to the proximal member and/or to the valve. The first end of the release member may be attached to the housing portion of the valve. The first end of the release member may be fixedly attached to the proximal member and/or to the valve. A second end of the release member may be movable relative to the proximal member. The second end of the release member may be axially movable relative to the proximal member. The second end of the release member may be slidingly movable relative to the proximal member. The release member may be movable relative to the distal member. The release member may be slidingly movable relative to the distal member.

In another aspect of the invention there is provided a wound retractor comprising:—
- a distal member for insertion through a wound opening;
- a proximal member for location externally of the wound opening;
- a connecting member extending at least between the distal member and the proximal member to retract laterally the sides of the wound opening; and
- a release member for releasing the distal member from a retracting configuration for removal of the distal member from the wound opening;
- the release member having a stowed configuration in which a proximal end of the release member terminates substantially adjacent to the proximal member.

Before the release member is required to be used to release the distal member, the release member is stowed away. By stowing the release member, this provides for a neat, simple wound retractor without the risk of the release member obstructing the surgeon's potentially limited working space.

In one embodiment of the invention the retractor comprises a valve. The valve may be mounted to the proximal member. The valve may be at least partially of a gelatinous elastomeric material. The valve may comprise a gelatinous elastomeric material portion and a housing portion. The housing portion may be mounted to the proximal member. The valve may comprise an opening extending therethrough. The opening may be biased towards a closed configuration. The opening may comprise a pinhole. The valve may be an instrument seal.

In another embodiment in the stowed configuration the proximal end of the release member is attached to the proximal member and/or to the valve. In the stowed configuration the proximal end of the release member may be releasably attached to the proximal member and/or to the valve. The release member may be movable from the stowed configuration to a deployed configuration. In the stowed configuration, at least part of the release member may be substantially concertinaed. In the deployed configuration the proximal end of the release member may extend proximally of the proximal member. In the deployed configuration, the proximal end of the release member may be detached from the proximal member and/or from the valve.

In a further embodiment in the retracting configuration, the distal member is located in a plane substantially perpendicular to the longitudinal axis of a wound opening. In the retracting configuration, the distal member may engage an inner wall of body tissue adjacent a wound opening. The release member may be pullable to release the distal member from the retracting configuration. A distal end of the release member may be attached to the distal member.

In one embodiment the connecting member extends in two layers between the distal member and the proximal member. The release member may extend between the two layers of the connecting member. The release member may extend around the two layers of the connecting member. The release member may be looped around the two layers of the connecting member.

In another embodiment at least part of the release member is substantially flexible. The release member may comprise a pull cord. The pull cord may comprise a ribbon. The release member may comprise a gripping portion. At least part of the gripping portion may be substantially rigid. The gripping portion may comprise a bead. The gripping portion may comprise a ring member. At least part of the gripping portion may be substantially flexible. The gripping portion may comprise a loop.

In another embodiment the connecting member comprises a sleeve. The sleeve acts to protect the sides of the retracted wound opening. The connecting member may have a proximal gripping portion for pulling the connecting member upwardly to shorten an axial extent located between the distal member and the proximal member. On release of the gripping portion the shortened axial extent between the distal member and the proximal member may be substantially maintained without a requirement for an additional locking device. The proximal gripping portion may be provided at a proximal end portion of the connecting member. The connecting member may be fixed to the proximal member at a first end portion and may be movable over the proximal member at a second end portion. The connecting member may be axially slidable over the proximal member at the second end portion. The second end portion of the connecting member may be slidingly received over a portion of the proximal member to allow relative movement between the connecting member and the proximal member to shorten the axial extent of the connecting member located between the distal member and the proximal member. The portion of the proximal member that slidingly receives the connecting member may include an outer portion of the proximal member. The second end portion of the connecting member may be biased against the proximal member. The proximal member may be located within the connecting member.

In one embodiment the proximal member forms a part of a securing arrangement configured to substantially fix the axial extent of the connecting member located between the distal member and the proximal member at a desired length. The connecting member may extend from the proximal member, around the distal member, and has a return section outside of the proximal member, the return section providing the proximal gripping portion. The distal member may comprise a distal ring. The distal ring may be an O-ring. The distal ring may be formed of an elastomeric material. The proximal member may comprise a proximal ring. The proximal ring may be an O-ring. The proximal ring may be relatively rigid with respect to the distal ring. The connecting member may be of a pliable material.

In another embodiment the retractor comprises a guide member for a proximal portion of the connecting member. The connecting member may extend between the guide member and the proximal member. The release member may extend at least partially between the guide member and the proximal member.

The release member may extend proximally substantially longitudinally into the space between the guide member and the proximal member. The release member may extend proximally substantially longitudinally out of the space between the guide member and the proximal member. The release member may extend proximally substantially transversely out of the space between the guide member and the proximal member. The release member may extend through an opening in a wall of the guide member. The guide member may comprise a receiver for the proximal member. The guide member may have an inwardly facing recess defining a receiver for the proximal member. The proximal member may comprise a proximal ring and the recess may have a shape which is complementary to that of the proximal ring. The recess may be substantially C-shaped in transverse cross section.

In another embodiment the retractor comprises a lock for locking the guide member to the proximal member. The guide member may be engageable with the proximal member to provide the lock.

In one case the invention provides a wound protector and retractor.

The invention also provides in another aspect a method of performing a surgical procedure, the method comprising the steps of:— inserting a distal member of a wound retractor through a wound opening;

locating a proximal member of the wound retractor externally of the wound opening, with a release member of the wound retractor in a stowed configuration with a proximal end of the release member terminating substantially adjacent to the proximal member;

retracting laterally the sides of the wound opening using a connecting member of the wound retractor;

releasing the distal member from a retracting configuration; and removing the distal member from the wound opening.

In one embodiment of the invention the method comprises the step of inserting an object through the retracted wound opening to access interior of the wound opening. The object may comprise an instrument. The retracted wound opening may be sealed. The method may comprise the step of inserting an object through the retracted wound opening while maintaining the retracted wound opening sealed.

In another embodiment a release member is pulled to release the distal member from the retracting configuration. The release member may be moved from the stowed configuration to a deployed configuration before releasing the distal member from the retracting configuration. The proximal end of the release member may be moved proximally relative to the proximal member to move the release member from the stowed configuration to the deployed configuration. The method may comprise the step of detaching the release member from the proximal member and/or from a valve.

In another embodiment the method comprises the step of gripping a portion of the connecting member and pulling the connecting member upwardly to shorten an axial extent of the connecting member located between the distal member and the proximal member. On release of the gripped portion the shortened axial extent of the connecting member between the distal member and the proximal member may be substantially maintained. The connecting member may be fixed to the proximal member at a first end portion and may extend over the proximal member at a second end portion, and the method may comprise the step of moving the connecting member over the proximal member as the connecting member is pulled upwardly to shorten the axial extent of the connecting member located between the distal member and the proximal member. The step of moving the connecting member relative to the proximal member may include sliding a portion of the connecting member against a radially outer portion of the proximal member.

In one case the retracted wound opening is of a size to receive an instrument. The connecting member may protect the sides of the retracted wound opening.

According to another aspect of the invention there is provided a wound retractor comprising:—
- a distal member for insertion through a wound opening;
- a proximal member for location externally of the wound opening;
- a connecting member extending at least between the distal member and the proximal member to retract laterally the sides of the wound opening; and
- a release member for releasing the distal member from a retracting configuration for removal of the distal member from the wound opening.

In one embodiment in the retracting configuration, the distal member is located in a plane substantially perpendicular to the longitudinal axis of a wound opening. In the retracting configuration, the distal member may engage an inner wall of body tissue adjacent a wound opening.

In one case the retractor comprises a valve. The valve may be mounted to the proximal member. The valve may be at least partially of a gelatinous elastomeric material. The valve may comprise a gelatinous elastomeric material portion and a housing portion. The housing portion may be mounted to the proximal member.

In one case the valve comprises an opening extending therethrough. The opening may be biased towards a closed configuration. The opening may comprise a pinhole. The valve may be an instrument seal.

In another embodiment the release member is pullable to release the distal member from the retracting configuration.

A distal end of the release member may be attached to the distal member. A proximal end of the release member may be attached to the proximal member and/or to the valve. The proximal end of the release member may be releasably attached to the proximal member and/or to the valve.

In another case the release member is movable from a stowed configuration to a deployed configuration. In the stowed configuration, at least part of the release member may be substantially concertinaed. In the stowed configuration, a proximal end of the release member may be attached to the proximal member and/or to the valve. In the deployed configuration, a proximal end of the release member may be detached from the proximal member and/or from the valve.

In another embodiment the release member extends in two layers between the distal member and the proximal member. The release member may be looped around the distal member. A first end of the release member may be attached to the valve. The first end of the release member may be attached to the housing portion. The first end of the release member may be fixedly attached to the valve.

In one case a second end of the release member is movable relative to the proximal member. The second end of the release member may be axially movable relative to the proximal member. The second end of the release member may be slidingly movable relative to the proximal member.

In another case the release member is movable relative to the distal member. The release member may be slidingly movable relative to the distal member.

In a further embodiment the connecting member extends in two layers between the distal member and the proximal member. The release member may extend between the two layers of the connecting member.

In another embodiment the release member extends around the two layers of the connecting member. The release member may be looped around the two layers of the connecting member.

At least part of the release member may be substantially flexible. The release member may comprise a pull cord. The pull cord may comprise a ribbon.

In a further case the release member comprises a gripping portion. At least part of the gripping portion may be substantially rigid. The gripping portion may comprise a bead. The gripping portion may comprise a ring member.

In one embodiment at least part of the gripping portion is substantially flexible. The gripping portion may comprise a loop.

In one case the connecting member comprises a sleeve. The connecting member may have a proximal gripping portion for pulling the connecting member upwardly to shorten an axial extent located between the distal member and the proximal member. On release of the gripping portion the shortened axial extent between the distal member and the proximal member may be substantially maintained without a requirement for an additional locking device. The proximal gripping portion may be provided at a proximal end portion of the connecting member.

In one case the connecting member is fixed to the proximal member at a first end portion and is movable over the proximal member at a second end portion. The connecting member may be axially slidable over the proximal member at a second end portion. The second end portion of the connecting member may be slidingly received over a portion of the proximal member to allow relative movement between the connecting member and the proximal member to shorten the axial extent of the connecting member located between the distal member and the proximal member. The portion of the proximal member that slidingly receives the connecting member may include an outer portion of the proximal member. The second end portion of the connecting member may be biased against the proximal member.

In one embodiment the proximal member is located within the connecting member.

The proximal member may form a part of a securing arrangement configured to substantially fix the axial extent of the connecting member located between the distal member and the proximal member at a desired length. The connecting member may extend from the proximal member, around the distal member, and may have a return section outside of the proximal member, the return section providing the proximal gripping portion.

In one case the distal member comprises a distal ring. The distal ring may be an O-ring. The distal ring may be formed of an elastomeric material.

The proximal member may comprise a proximal ring. The proximal ring may be an O-ring. The proximal ring may be relatively rigid with respect to the distal ring.

In one case the connecting member is of a pliable material.

The retractor may comprise a guide member of a proximal portion of the connecting member. The connecting member may extend between the guide member and the proximal member. The release member may extend between the guide member and the proximal member. The guide member may comprise a receiver for the proximal member. The guide member may have an inwardly facing recess defining a receiver for the proximal member. The proximal member may comprise a proximal ring and the recess may have a shape which is complementary to that of the proximal ring. The recess may be substantially C-shaped in transverse cross section.

In one case the retractor comprises a lock for locking the guide member to the proximal member. The guide member may be engagable with the proximal member to provide the lock.

The invention provides in once case a wound protector and retractor.

In another aspect of the invention, there is provided a method of performing a surgical procedure, the method comprising the steps of:—
- inserting a distal member of a wound retractor through a wound opening;
- locating a proximal member of the wound retractor externally of the wound opening;
- retracting laterally the sides of the wound opening using a connecting member of the wound retractor;
- releasing the distal member from a retracting configuration; and
- removing the distal member from the wound opening.

In one embodiment of the invention the method comprises the step of inserting an object through the retracted wound opening to access interior of the wound opening. The object may comprise an instrument.

In one case the retracted wound opening is sealed. The method may comprise the step of inserting an object through the retracted wound opening while maintaining the retracted wound opening sealed.

In one embodiment a release member is pulled to release the distal member from the retracting configuration.

The release member may be moved from a stowed configuration to a deployed configuration before releasing the distal member from the retracting configuration. The release member may be detached from the proximal member and/or from a valve.

In another case the method comprises the step of gripping a portion of the connecting member and pulling the connecting member upwardly to shorten an axial extent of the connecting member located between the distal member and the proximal member. On release of the gripped portion the shortened axial extent of the connecting member between the distal member and the proximal member may be substantially maintained. The connecting member may be fixed to the proximal member at a first end portion and may extend over the proximal member at a second end portion, and the method may comprise the step of moving the connecting member over the proximal member as the connecting member is pulled upwardly to shorten the axial extent of the connecting member located between the distal member and the proximal member. The step of moving the connecting member relative to the proximal member may include sliding a portion of the connecting member against a radially outer portion of the proximal member.

In a further case the retracted wound opening is of a size to receive an instrument.

The connecting member may protect the sides of the retracted wound opening.

According to the invention there is also provided a medical device comprising:—
- a retractor member comprising a distal portion for insertion through an incision made in a patient, and a proximal portion for extending from the incision and outside of the patient;
- a distal member associated with the distal portion of the retractor member;
- a proximal member associated with the proximal portion of the retractor member;
- the retractor member being axially movable relative to the proximal member to draw the proximal and distal members towards one another thereby shortening the axial extent of the retractor member between the proximal and distal members.

In one embodiment the retractor member comprises a sleeve member. The sleeve member preferably extends around the distal member.

In one embodiment the distal member is a ring member such as a resilient ring member, for example, an O-ring.

In one embodiment the proximal member is connected to the retractor member. The proximal member may be a ring member.

In one embodiment the sleeve is of a pliable material.

In one arrangement the sleeve extends from the proximal member, around the distal member and has a return section outside of the proximal member.

In one embodiment the device comprises a guide member. The retractor member may extend between the guide member and the proximal member.

The guide member may comprise a receiver for the proximal member.

The guide member may comprise a guide ring-receiving member.

In another embodiment the sleeve return section is mounted to the guide member.

The sleeve return section may be extended into the opening defined by the guide member.

The device may comprise a lock for locking the guide member to the proximal member. Typically the guide member is engagable with the proximal member to provide the lock.

In one embodiment of the invention the device includes a valve.

In one embodiment the device comprises a release member for releasing the device from an incision. The release member may comprise an elongate member such as a pull ribbon or string extending from a distal end of the device.

The release member may extend from the distal member.

The invention also provides a method for retracting an incision comprising the steps of:—
- providing a device comprising a retractor member having a distal portion and a proximal portion, a distal member associated with the distal portion and a proximal member associated with the proximal portion;
- inserting the distal member and the distal portion of the retractor member through an incision made in a patient; and
- pulling the retractor member axially relative to the proximal member to draw the proximal and distal members towards one another thereby shortening the axial extent of the retractor member between the proximal and distal members and retracting the incision.

BRIEF DESCRIPTION OF THE DRAWINGS

The invention will be more clearly understood from the following description of some embodiments thereof, given by way of example only, with reference to the accompanying drawings, in which:—

FIGS. 6 to 8 are views similar to FIGS. 1 to 3 of another wound retractor according to the invention;

FIG. 9 is a view similar to FIG. 1 of a further wound retractor according to the invention;

FIGS. 10 to 12 are cross-sectional, side views of another wound retractor according to the invention, in use;

FIGS. 13 to 15 are views similar to FIGS. 10 to 12 of a further wound retractor according to the invention, in use;

FIG. 16 is a perspective view of another wound retractor according to the invention; and FIGS. 17 to 19 are cross-sectional, side views of the wound retractor of FIG. 16, in use.

DETAILED DESCRIPTION

Figure 1:
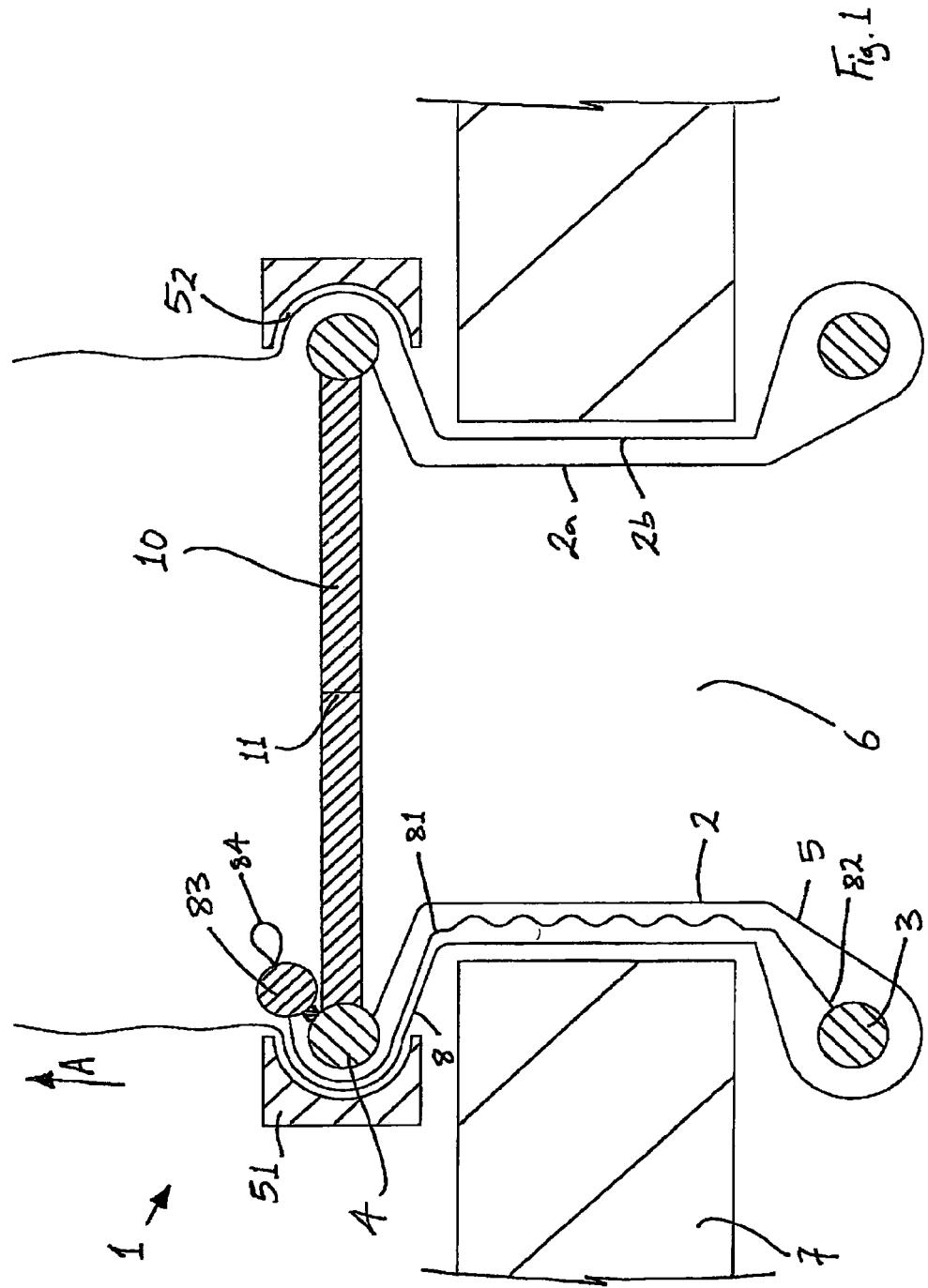
FIG. 1 is a cross-sectional, side view of a wound retractor according to the invention.

Referring to the drawings, and initially to FIGS. 1 to 4 thereof, there is illustrated a wound retractor 1 according to the invention, which comprises a retractor member provided by a sleeve 2, an elastomeric distal member provided by a distal ring 3 of resilient material such as an O-ring, and a relatively rigid proximal member provided by a proximal ring 4 which may also be an O-ring. The distal member 3 is suitable for insertion through a wound opening or incision 6, and the proximal member 4 is suitable for location externally of the wound opening/incision 6.

The sleeve 2 is of any suitable material such as of pliable plastics film material and comprises a distal portion 5 for insertion through the incision 6, in this case made in a patient's abdomen 7, and a proximal portion 8 for extending from the incision 6 and outside of the patient.

In this case the distal ring 3 is not fixed to the sleeve 2 but rather the sleeve 2 is led around the ring 3 and is free to move axially relative to the distal ring 3 somewhat in the manner of a pulley. The proximal ring 4 is fixed to the sleeve 2, in this case at the proximal inner end thereof.

To configure the wound retractor 1 according to the invention, the sleeve 2 is first provided with the proximal ring 4 fixed at one end of the sleeve 2. The distal ring 3 is then placed over the sleeve 2, and the sleeve 2 is manipulated so that the sleeve 2 is folded back on itself into the configuration of FIG. 1. The sleeve 2 extends from the proximal ring 4, and the distal ring 3 is contained between inner and outer layers 2a, 2b of the sleeve 2. The wound retractor 1 is now ready for use.

The resilient distal ring 3 is scrunched up and inserted through the incision 6 with the distal end 5 of the sleeve 2. The sleeve 2 is then pulled upwardly in the direction of the arrow A in FIG. 1. On pulling of the sleeve 2 upwardly, the outer layer 2b is pulled up while the inner layer 2a is drawn around the distal ring 3. This results in shortening of the axial extent of the sleeve 2 between the proximal ring 4 and the distal ring 3, tensioning the sleeve 2 and applying a retraction force to the margins of the incision 6. The wound retractor 1 appears to be self locking because when tension is applied to the sleeve 2 and the pulling force is released the rings 3, 4 remain in position with a retraction force applied. Frictional engagement between the layers 2a, 2b of the sleeve 2 in this retracting configuration may contribute to this self locking.

In this retracting configuration, the distal ring 3 lies in a horizontal plane perpendicular to the longitudinal axis of the wound opening 6, and the distal ring 3 engages the inner wall of the abdomen 7 around the edges of the wound opening 6.

As the incision 6 is being retracted the margins are also protected by the sleeve 2. On retraction, an access port is provided, for example for a surgeon to insert an instrument to perform a procedure. The wound retractor 1 is used as a retractor and as a base for a valve/seal 10 to allow it to be used in laparoscopic surgery or for instrument access generally. In this case the valve 10 comprises a gelatinous elastomeric material mounted to the proximal ring 4. The valve 10 has a pinhole opening 11 extending therethrough through which an object, such as an instrument, may be inserted to access the interior of the abdomen 7. The opening 11 is biased towards a closed configuration to maintain the interior of the abdomen 7 sealed and to minimise gas pressure leakage through the valve 10.

The valve 10 may be of any suitable configuration, for example in the form of a valve similar to the valves described in International patent applications published under Nos. WO 2005/044111 and WO 2005/034766, the relevant contents of which are incorporated herein by reference.

Any excess sleeve portion outside the incision 6 may, for example, be cut-away.

The wound retractor 1 is suitable for a range of incision sizes and is easily manufactured. It is also relatively easy to manipulate, in use. It not only retracts but also protects the incision 6.

The wound retractor 1 also comprises a guide member 51 for the proximal ring 4. The guide member 51 is in the form of an annular ring member with an inwardly facing C-shaped groove 52 which is sized to accommodate the proximal ring 4, as illustrated in FIG. 1. The outer layer 2b of the sleeve 2 is interposed between the proximal ring 4 and the guide member 51 to further control the pulling of the sleeve 2 and thereby further controlling the application of the retraction force. The guide member 51 also assists in stabilising the proximal ring 4.

Any suitable guide such as the guide member 51 may be used to assist in retaining/stabilising the proximal ring 4 in a desired position during pulling up of the sleeve 2 to retract the incision 6. The guide may be located proximal of the ring 4.

The guide member 51 provides a mounting member to which devices such as valves may be attached.

The wound retractor 1 also has a release mechanism which in this case is provided by a flexible release pull cord or ribbon 81 which is attached at one end 82 to the inner ring 3 and terminates in a rigid bead 83 at the opposite end. The bead 83 may be gripped by a user.

Figure 3:
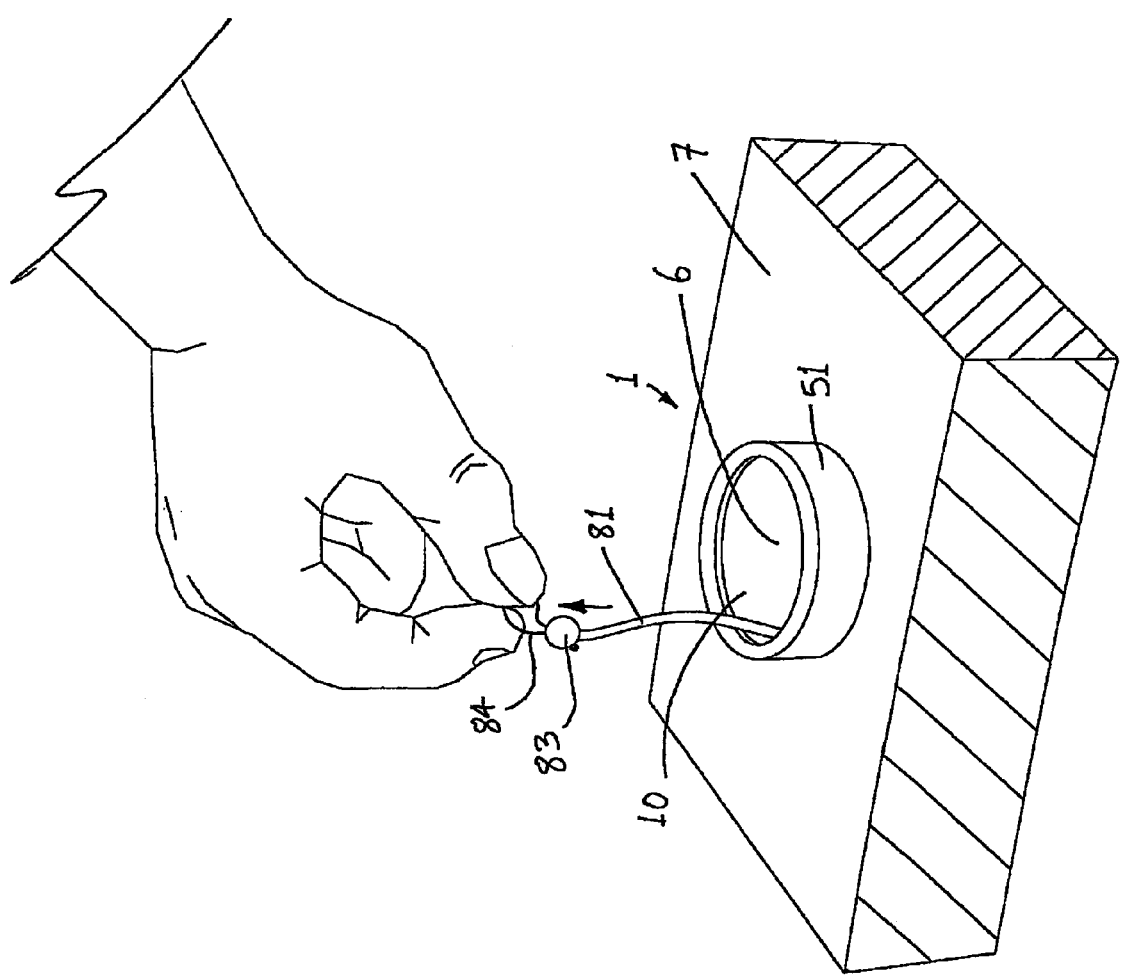
Figure 4:
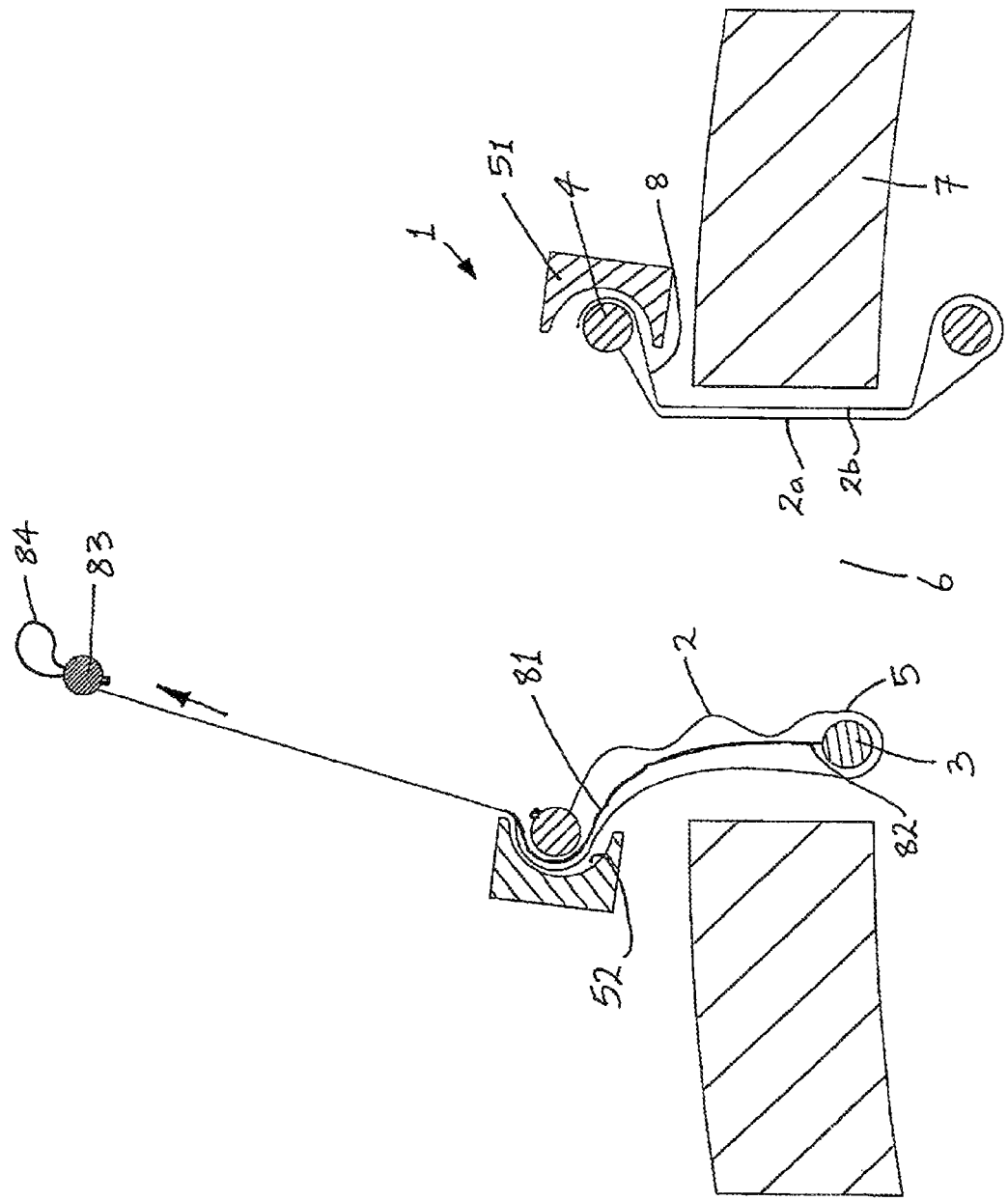
FIG. 4 is a cross-sectional, side view of the wound retractor of FIG. 1, in use.

The ribbon 81, on assembly, is led through the gap between the proximal ring 4 and the guide member 51 so that it is positioned between the proximal ring 4 and the guide member 51 and is positioned between the inner and outer layers 2a, 2b of the sleeve 2. The ribbon 81 facilitates release of the distal ring 3 from the retracting configuration in the incision 6. Pulling on the ribbon 81 pulls on the distal ring 3, allowing the distal ring 3 to be released from the inner wall of the incision 6 to thereby release the wound retractor 1 (FIGS. 3 and 4). The flexibility of the distal ring 3 facilitates this movement. The distal ring 3 and the sleeve 2 may then be remove from the wound opening 6.

The advantage of this arrangement is that a user can readily release the wound retractor 1 from the self locked retracting configuration.

Figure 2:
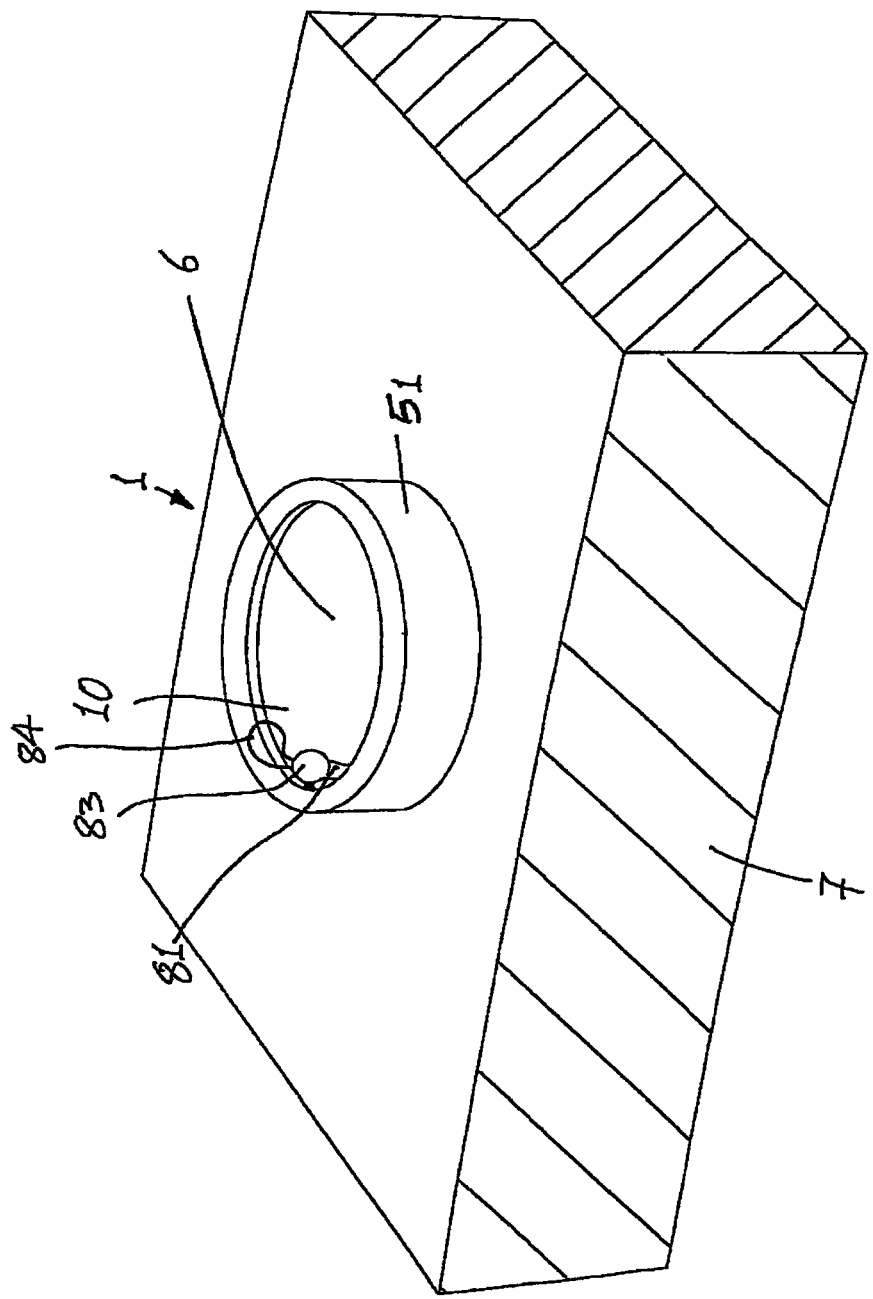
FIGS. 2 and 3 are perspective views of the wound retractor of FIG. 1, in use.

The ribbon 81 has a stowed configuration, illustrated in FIGS. 1 and 2, and a deployed configuration, illustrated in FIGS. 3 and 4. In the stowed configuration, the bead 83 at the proximal end of the ribbon 81 terminates adjacent to the proximal ring 4. In the stored configuration the bead 83 is releasably attached to the proximal ring 4, and the ribbon 81 is concertinaed. To move the ribbon 81 from the stowed configuration to the deployed configuration, the bead 83 at the proximal end of the ribbon 81 is moved proximally relative to the proximal ring 4. In the deployed configuration, the ribbon 81 is pulled taut and the bead 83 at the proximal end of the ribbon 81 extends proximally of the proximal ring 4. In the deployed configuration, the bead 83 is detached from the proximal ring 4.

A flexible loop 84 on the bead 83 may be used to grip the release member.

In use, the wound opening 6 is created in the abdomen 7. The distal ring 3 is scrunched up and inserted through the wound opening 6, and the proximal ring 4 is located externally of the wound opening 6. The sleeve 2 extends between the proximal ring 4 and the distal ring 3. The proximal end of the sleeve 2 is then pulled upwardly to shorten the axial extent of the sleeve 2 between the proximal ring 4 and the distal ring 3 to retract laterally the sides of the wound opening 6. When the wound opening 6 has been retracted the desired amount, the proximal end of the sleeve 2 is released by the user and the wound retractor 1 remains locked in this retracting configuration (FIG. 1).

It is noted that in this retracting configuration, the ribbon 81 is concertinaed and the bead 83 is attached to the proximal member 4 in the stowed configuration. In this stowed configuration the ribbon 81 does not extend proximally past the proximal ring 4. Thus the ribbon 81 will not obstruct access to the wound interior through the retracted wound opening 6.

FIG. 1 shows how the majority of the ribbon/tie component 81 remains below the skin surface when not in use. There is a temporary fix means on the bead 83 or ribbon section 81 to hold it in place until needed. The temporary fix prevents the ribbon 81 following the sleeve 2 up during deployment. The ribbon 81 for removing the distal ring 3 is compressed in a concertina manner into the lower part of the retracting sleeve 2. The bead 83 or similar stop component prevents loss of access to the ribbon/tie 81 in case it entirely slips downward. There is a means to grip the ribbon tie 81 with either fingertips or hooking instrument, this means may be similar to the loop 84 illustrated in FIG. 2. The bead 83 is temporarily fixed to the proximal O-ring 4 in FIG. 2.

An object, such as an instrument may be inserted through the pinhole opening 11 in the valve 10 and through the retracted wound opening 6 to access the interior of the abdomen 7. The self-closing pinhole 11 maintains a seal around the instrument passed through the valve 10.

When the surgical procedure has been completed and it is desired to remove the wound retractor 1 from the retracted wound opening 6, the bead 83 is detached from the proximal member 4 and pulled upwardly to draw the ribbon 81 taut (FIG. 3). FIG. 3 shows how the ribbon/tie 84 can be grabbed by the fingertips when the surgeon is ready to take the distal ring 3 out of the incision 6. In FIG. 3, the temporary fix is broken. Further pulling of the bead 83 upwardly releases the distal ring 3 from the retracting configuration, and thus releases the wound retractor 1 to enable the distal ring 3 and the sleeve 2 to be removed from the wound opening 6 (FIG. 4). FIG. 4 shows how the ribbon tie 81 is connected to the distal ring 3 inside the incision 6. When pulled upwards, the ribbon 81 causes the distal ring 3 to buckle and become dislodged from the incision 6.

Figure 5:
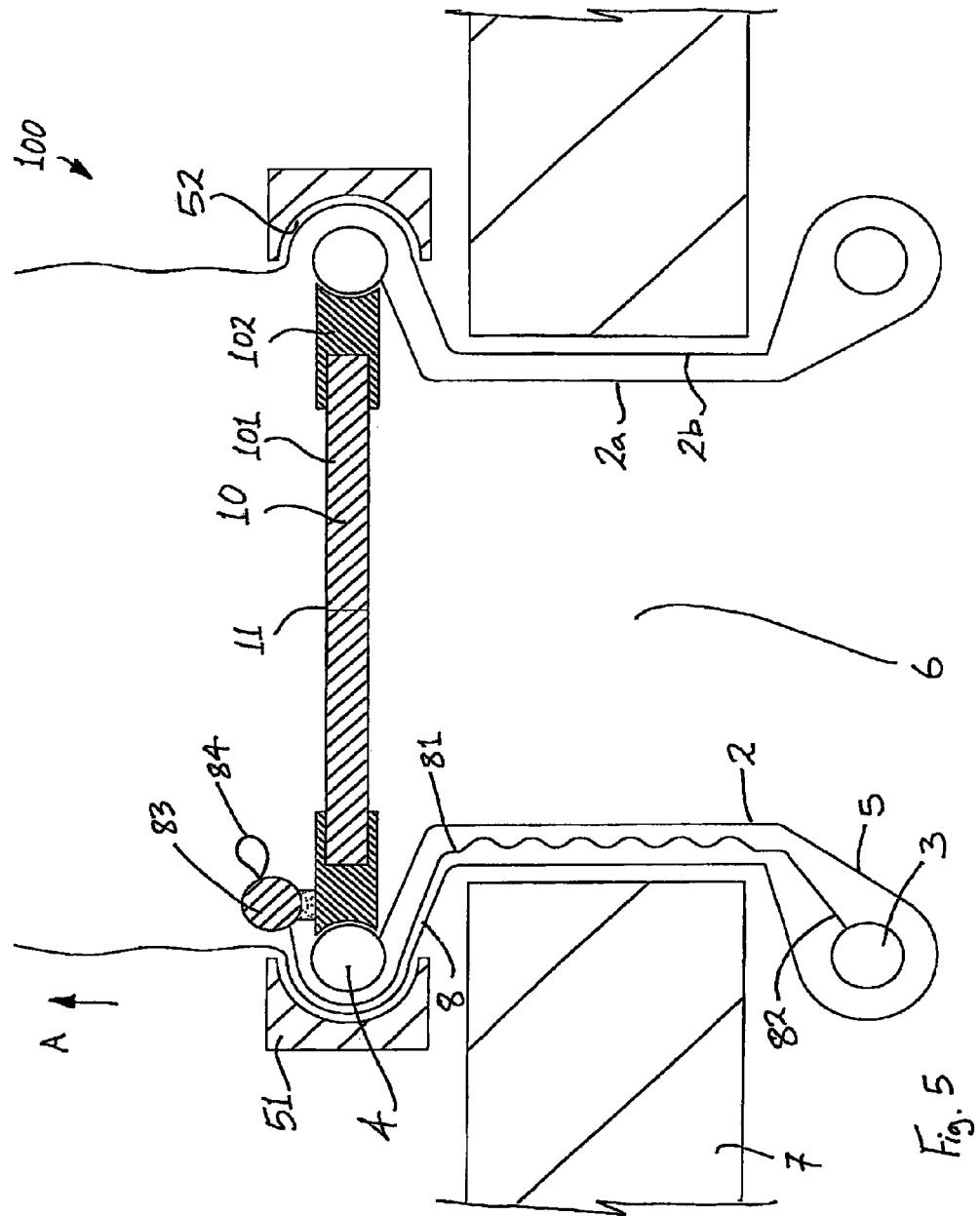
FIG. 5 is a view similar to FIG. 1 of another wound retractor according to the invention.

In FIG. 5 there is illustrated another wound retractor 100 according to the invention, which is similar to the wound retractor 1 of FIGS. 1 to 4, and similar elements in FIG. 5 are assigned the same reference numerals.

In this case, the valve 10 comprises a gelatinous elastomeric portion 101 and a housing portion 102 radially outwardly of the gelatinous elastomeric portion 101. The housing portion 102 is mounted to the proximal ring 4. In the stowed configuration illustrated in FIG. 5, the bead 83 is releasably attached to the housing portion 102.

Figure 6:
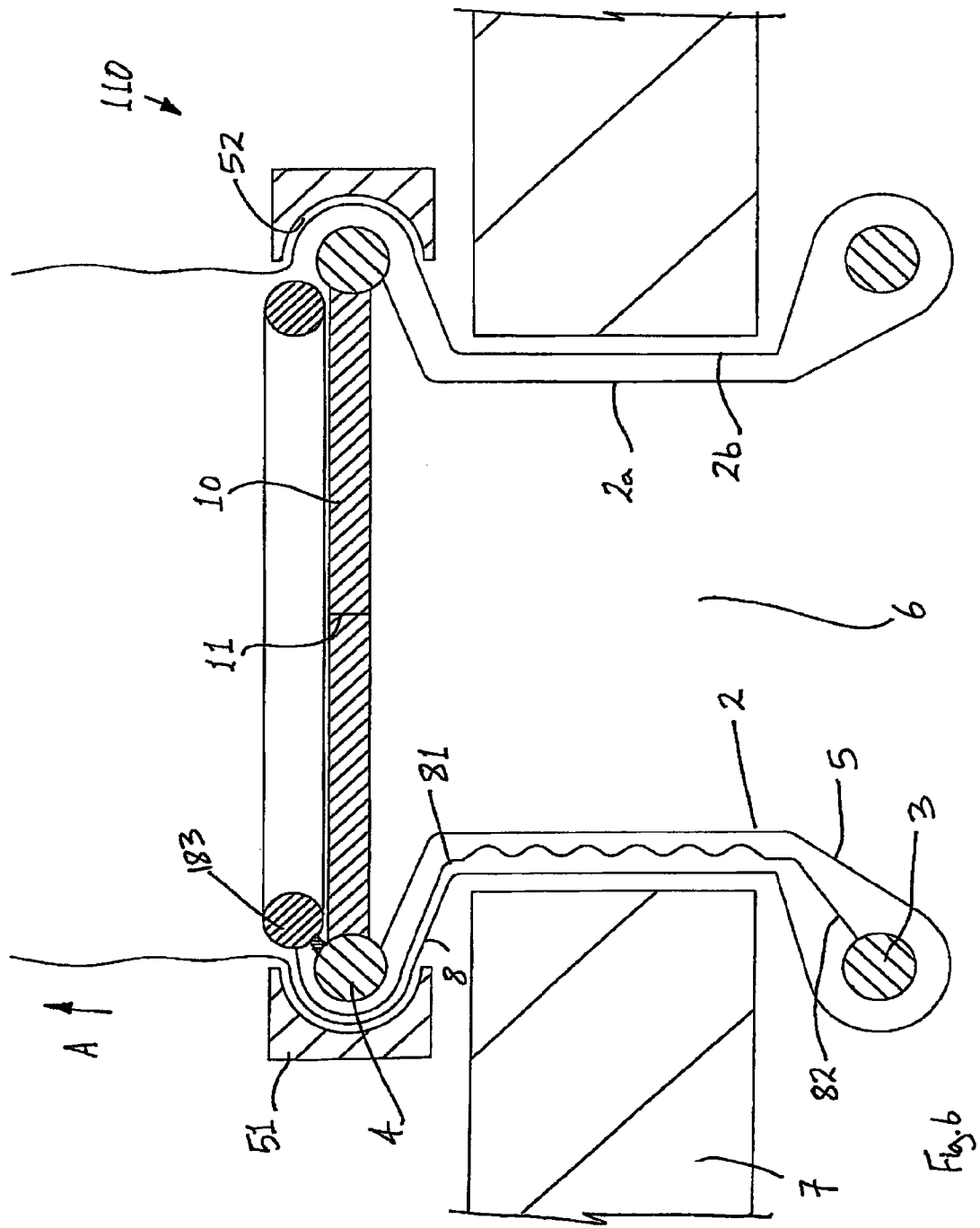

FIGS. 6 to 8 illustrate another wound retractor 110 according to the invention, which is similar to the wound retractor 1 of FIGS. 1 to 4, and similar elements in FIGS. 6 to 8 are assigned the same reference numerals.

In this case the release member comprises the ribbon 81 and a ring member 183 attached to the proximal end of the ribbon 81. In the stowed configuration illustrated in FIG. 6, the ring member 183 lies on top of the valve 10 in a plane perpendicular to the longitudinal axis of the wound opening 6, and the ring member 183 is releasably attached to the proximal ring 4. FIG. 6 shows how the ring removal device 183 may be integrated into the valve housing. There is a temporary fix of the ring member 183 to the proximal ring 4.

After completion of a surgical procedure, the ring member 183 may be detached from the proximal ring 4 (FIG. 7) and pulled upwardly to release the distal ring 3 from the retracting configuration (FIG. 8). FIG. 8 shows how the ring 183 can be dislodged from the housing and used to lever the internal distal ring 3 out of the incision 6.

FIGS. 6 to 8 show the same idea as the bead 83 but instead using a ring 183 that can be neatly integrated into the valve housing, and easily gripped by a fingertip.

Referring to FIG. 9, there is illustrated a further wound retractor 120 according to the invention, which is similar to the wound retractor 100 of FIG. 5, and similar elements in FIG. 9 are assigned the same reference numerals.

In this case the release member comprises the ribbon 81 and a ring member 183 attached to the proximal end of the ribbon 81. In the stowed configuration illustrated in FIG. 9, the ring member 183 lies on top of the valve 10 in a plane perpendicular to the longitudinal axis of the wound opening 6, and the ring member 183 is releasably attached to the housing portion 102.

After completion of a surgical procedure, the ring member 183 may be detached from the housing portion 102 and pulled upwardly to release the distal ring 3 from the retracting configuration.

In FIGS. 10 to 12 there is illustrated another wound retractor 300 according to the invention, which is similar to the wound retractor 100 of FIG. 5, and similar elements in FIGS. 10 to 12 are assigned the same reference numerals.

In this case the ribbon 81 extends in two layers between the proximal ring 4 and the distal ring 3 through the wound opening 6. In particular a first end 301 of the ribbon 81 is fixedly attached to the housing portion 102 of the valve 10, and a second end 302 of the ribbon 81 is slidingly movable relative to the proximal ring 4 and the guide member 51. The ribbon 81 extends distally from the first end 301 to the distal ring 3, loops around the distal ring 3, extends proximally from the distal ring 3 between the guide member 51 and the proximal ring 4 to the second end 302. In particular the ribbon 81 extends proximally longitudinally into the space between the guide member 51 and the proximal ring 4, through the space between the guide member 51 and the proximal ring 4, and longitudinally out of the space between the guide member 51 and the proximal ring 4 (FIG. 10).

The ribbon 81 is looped around the two layers 2a, 2b of the sleeve 2.

When pulled the ribbon 81 is axially movable between the guide member 51 and the proximal ring 4, and the ribbon 81 is slidingly movable relative to the distal ring 3 (FIG. 12).

In the configuration of FIGS. 10 to 12 the ribbon/cord 81 is attached to the underside of the gel housing 102 and passes around the distal ring 3 and beyond the outer proximal ring 51. A simple upward lift of the ribbon 81 is all that is needed to release the distal O-ring 3 (FIG. 12).

FIGS. 13 to 15 illustrate a further wound retractor 310 according to the invention which is similar to the wound retractor 300 of FIGS. 10 to 12, and similar elements in FIGS. 13 to 15 are assigned the same reference numerals.

In this case the ribbon 81 does not extend between the guide member 51 and the proximal ring 4. As illustrated, the ribbon 81 extends distally from the first end 301 to the distal ring 3, loops around the distal ring 3, extends proximally from the distal ring 3 to the second end 302.

The ribbon 81 extends in two layers through the wound opening 6.

The fixed end of the removal ribbon 81 is attached to the underside of the gel housing 102.

FIG. 14 illustrates the wound retractor 310 after it has been deployed. Any slack or excess ribbon 81 may be gently used up by lightly tugging on the free end 302 of the ribbon 81.

To remove the wound retractor 310, a user pulls on the free end 302 of the ribbon 81. This deforms the distal ring 3 and drags it out through the incision 6 (FIG. 15).

Referring to FIGS. 16 to 19 there is illustrated another wound retractor 320 according to the invention, which is similar to the wound retractor 300 of FIGS. 10 to 12, and similar elements in FIGS. 16 to 19 are assigned the same reference numerals.

In this case a slot opening 321 is provided in the wall of the guide member 51.

Figure 17:
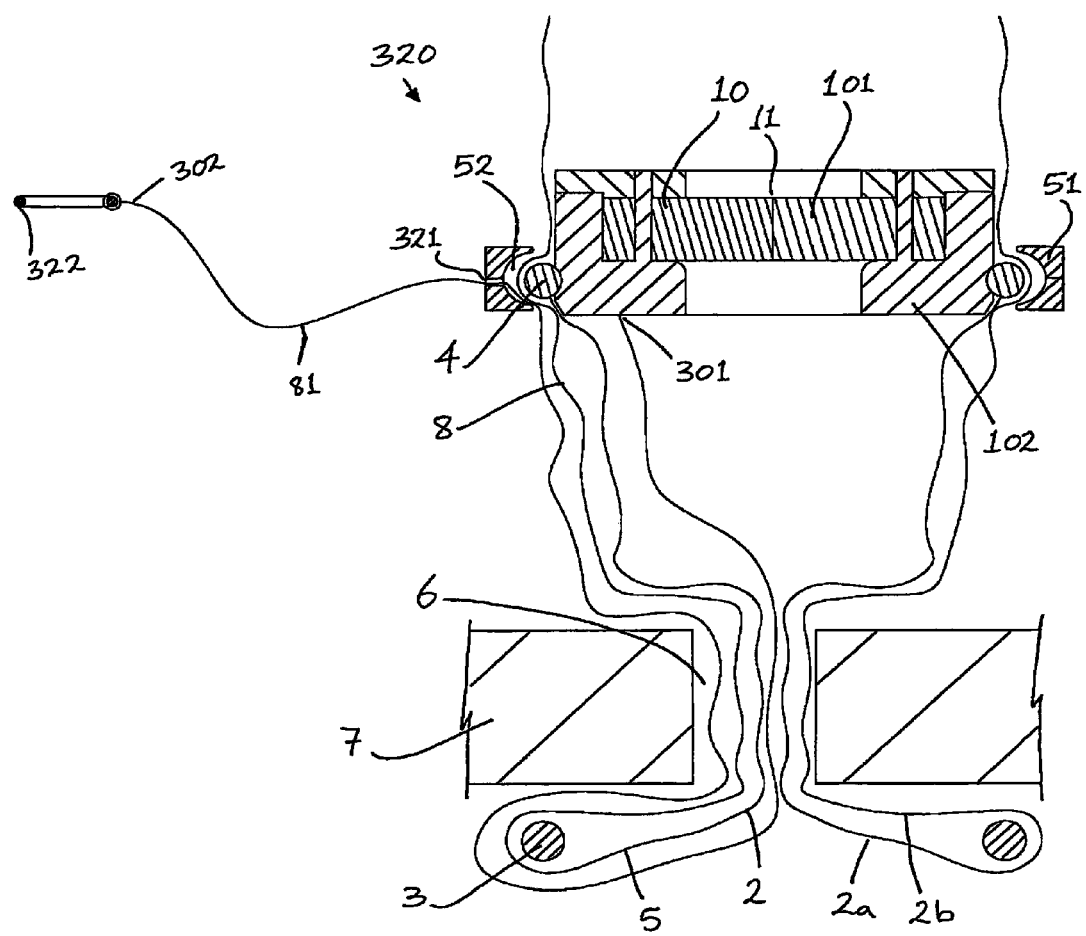

The ribbon 81 extends distally from the first end 301 to the distal ring 3, loops around the distal ring 3, extends proximally from the distal ring 3 between the guide member 51 and the proximal ring 4 to the second end 302. As illustrated in FIG. 17 the ribbon 81 extends proximally longitudinally into the space between the guide member 51 and the proximal ring 4 through part of the space between the guide member 51 and the proximal ring 4, and transversely out of the space between the guide member 51 and the proximal ring 4 through the slot opening 321.

A rigid ring member 322 is fixedly attached to the ribbon 81 at the second end 302.

In further detail, FIG. 16 illustrates the pull ring 322, the ribbon 81, the slot 321 for the ribbon 81, the outer proximal ring 51, and the sleeve 2. FIG. 17 illustrates the removal ring 322, the ribbon 81, and the slot 321 for the ribbon 81. FIG. 19 illustrates removal of the wound retractor 320 after completion of the surgical procedure.

It will be appreciated that the connecting member extending between the distal member and the proximal member may be provided in any suitable form, such as in the form of one or more straps.

The wound retractor of the invention can be used in a number of ways. In one method the wound retractor is used as described above with the distal ring being inserted into an incision and the proximal ring being slid to controllably radially expand the incision. The wound retractor may then be locked in position. If necessary, the proximal ring can be moved further downwardly to create a larger incision.

In some arrangements an instrument may be bent manually outside the body and the bent instrument is delivered through the wound retractor to readily access the operative site.

In a further embodiment an instrument is inserted into the wound retractor and the surgeon uses the abdominal wall itself to bend the instrument and then insert the bent section further into the abdomen.

In all cases the sleeve may be gripped by gripping a valve or other element mounted thereto.

The wound retractor of the invention has at least some of the following advantages:
Controlled Radial Expansion
1. Greater access using smaller incision
2. Can vary incision size as need be (e.g. specimen removal during lap coli.)
Greater Sealing Capabilities
1. No gas leakage from the wound margins
2. Cannot be inadvertently pulled out of the incision
3. Will seal any incision and never require secondary sealing method (suture, Hasson port, etc.)
Eliminate Intra-abdominal Profile
1. Gives back more working space in the abdomen (critical in pelvic surgery)
2. Perineal access for operations such as Radical Prostatectomy.
Protection of Wound from Infection and Cancer Seeding
1. Tight seal with no "chimney stack" effect
2. Upon removal all areas of potential contamination are isolated from the incision
Reduced Extra-abdominal Profile
1. Will increase the effective working length of an instrument
2. Greater working area outside the abdomen
Increase the Freedom of Movement of Conventional Laparoscopic Instruments The invention is not limited to the embodiments hereinbefore described, with reference to the accompanying drawings, which may be varied in construction and detail.

The invention claimed is:

1. A surgical wound retracting device, comprising:
a resilient distal ring;
a proximal ring;
a wound retracting sleeve configured to contact and retract the wound when the device is in use, the wound retracting sleeve extending at least between the proximal ring and the distal ring;
an outer radial member; and
a release member located radially within a portion of the wound retracting sleeve, and extending between the proximal ring and the outer radial member, wherein when the release member is in use, a pulling force on the release member applies a pulling force on the distal ring to assist in removing the device from a patient.

2. The surgical wound retracting device of claim 1, wherein the release member is secured by engagement between the proximal ring and the outer radial member.

3. The surgical wound retracting device of claim 1, wherein the release member extends at least from around the distal ring proximally to the proximal ring.

4. The surgical wound retracting device of claim 1, wherein the release member loops around the distal ring.

5. The surgical wound retracting device of claim 1, wherein the release member is configured to slidably engage the proximal ring and the outer radial member.

6. The surgical wound retracting device of claim 1, further including a valve assembly configured to seal an access opening through the wound retracting sleeve.

7. A wound retracting device, comprising:
a distal ring;
a proximal ring;
a wound retracting sleeve configured to contact and exert a retracting force on the wound when the device is in use, the wound retracting sleeve extending at least from the proximal ring to the distal ring;
a proximal member assisting in controlling the retracting force exerted by the wound retracting sleeve when the device is in use; and
a release member, including a cord, extending from the distal ring proximally to the proximal ring, and extending between the proximal ring and the proximal member.

8. The wound retracting device of claim 7, wherein the release member is secured between the proximal ring and the proximal member.

9. The wound retracting device of claim 7, wherein the release member extends around the distal ring.

10. The wound retracting device of claim 7, wherein the release member is configured to slidably engage the proximal ring and the proximal member.

11. The wound retracting device of claim 7, further including a valve assembly configured to seal an access opening through the wound retracting sleeve.

12. A wound retracting device, comprising:
a distal ring;
a proximal assembly, including:
an inner radial member, and
an outer radial member;
a wound retracting sleeve configured to contact and retract the wound when the device is in use, the wound retracting sleeve extending at least from the proximal assembly to the distal ring; and
a release member extending from the distal ring proximally to the proximal assembly, then between the inner radial member and the outer radial member, and then out from between the inner radial member and the outer radial member.

13. The wound retracting device of claim 12, wherein the outer radial member includes an opening, and the inner radial member extends at least partially through the opening.

14. The wound retracting device of claim 12, wherein the release member slidably engages the inner radial member and the outer radial member.

15. The wound retracting device of claim 12, wherein the proximal assembly includes a valve assembly configured to seal an access opening through the wound retracting sleeve.

16. The wound retracting device of claim 12, wherein a portion of the release member extending out from between the inner radial member and the outer radial member is coupled to an enlarged gripping member.

17. The surgical wound retracting device of claim 1, wherein the release member includes a cord.

18. The surgical wound retracting device of claim 12, wherein the release member includes a cord.

* * * * *